(12) United States Patent
Viscarra Rossel et al.

(10) Patent No.: US 10,845,353 B2
(45) Date of Patent: Nov. 24, 2020

(54) SOIL CONDITION ANALYSIS SYSTEM AND PROCESS

(71) Applicant: Commonwealth Scientific and Industrial Research Organisation, Acton, Australian Capital Territory (AU)

(72) Inventors: Raphael Viscarra Rossel, Acton (AU); Paul Flick, Pullenvale (AU); Craig Raymond Lobsey, Acton (AU)

(73) Assignee: Commonwealth Scientific and Industrial Research Organisation, ACT (AU)

( * ) Notice: Subject to any disclaimer, the term of this patent is extended or adjusted under 35 U.S.C. 154(b) by 221 days.

(21) Appl. No.: 15/736,962

(22) PCT Filed: Jun. 15, 2016

(86) PCT No.: PCT/AU2016/050500
§ 371 (c)(1),
(2) Date: Dec. 15, 2017

(87) PCT Pub. No.: WO2016/201508
PCT Pub. Date: Dec. 22, 2016

(65) Prior Publication Data
US 2018/0188225 A1 Jul. 5, 2018

(30) Foreign Application Priority Data

Jun. 15, 2015 (AU) .................... 2015902264

(51) Int. Cl.
*G01N 33/24* (2006.01)
*G01N 1/08* (2006.01)
(Continued)

(52) U.S. Cl.
CPC ............... *G01N 33/24* (2013.01); *G01N 1/08* (2013.01); *G01N 23/223* (2013.01); *G01N 23/2204* (2013.01); *G01N 23/04* (2013.01)

(58) Field of Classification Search
CPC .......... G01N 33/24; G01N 1/08; G01N 23/04; G01N 23/2204; G01N 23/223
See application file for complete search history.

(56) References Cited

U.S. PATENT DOCUMENTS

| 2014/0218716 A1 | 8/2014 | Brown et al. |
| 2015/0347647 A1* | 12/2015 | Osborne ................. B09C 1/002 703/6 |
| 2017/0223947 A1* | 8/2017 | Gall .................... G01N 21/4738 |

OTHER PUBLICATIONS

European Search Report for EP Application No. 16810620.1 dated Mar. 8, 2019 (8 pages).

(Continued)

*Primary Examiner* — Bryan Bui
(74) *Attorney, Agent, or Firm* — Merchant & Gould P.C.

(57) ABSTRACT

A soil condition analysis system, including: a support platform to support an elongate soil core extracted from the Earth; a plurality of soil sensing components configured to measure corresponding characteristics of a soil core supported on the support platform; one or more data acquisition components in communication with the soil sensing components and configured to generate measurement data representing the measured characteristics from the soil sensing components; wherein at least one of the support platform and the plurality of soil sensing components is mounted on a computer-controlled translation stage to enable the soil sensing components to automatically measure the corresponding characteristics of the soil core at mutually spaced locations along a longitudinal axis of the elongate soil core. The system includes a data processing and data analytics component configured to process the measurement data to (Continued)

generate soil property data representing corresponding soil properties of the elongate soil core as a function of depth, based on mathematical and statistical methods.

20 Claims, 27 Drawing Sheets

(51) Int. Cl.
    *G01N 23/223*     (2006.01)
    *G01N 23/2204*     (2018.01)
    *G01N 23/04*     (2018.01)

(56) References Cited

OTHER PUBLICATIONS

Rossel: "Soil carbon measurement revolution." Carbon Conference (Mar. 18, 2014) pp. 1-32.

Ross et al. "A multi-sensor logger for rock cores: Methodology and preliminary results from the Matagami mining camp, Canada." Ore Geology Reviews, vol. 53 (Sep. 1, 2013) pp. 93-111.

International Search Report for PCT/AU2016/050500 dated Sep. 15, 2016 (3 pages).

Viscarra. "Soil Carbon Measurement (r)evolution." Carbon Conference, Mar. 18, 2014. (32 pages).

Unknown. "Geotek Multi-Sensor Core Logger" retrieved from the Internet on Sep. 9, 2016, http://www.geotek.co.uk/products/mscl-s published Oct. 18, 2009 as per Wayback Machine. (3 pages).

Hewson et al. "Investigations into Soil Composition and Texture Using Infrared Spectroscopy (2-14um)." Hindawi Publishing Corporation, Applied and Environmental Soil Science, vol. 2012, (Aug. 2012) 12 pages.

Viscarra et al. "Proximal Soil Sensing: An Effective Approach for Soil Measurements in Space and Time." Advances in Agronomy, vol. 113, Dec. 2011, pp. 1-48.

\* cited by examiner

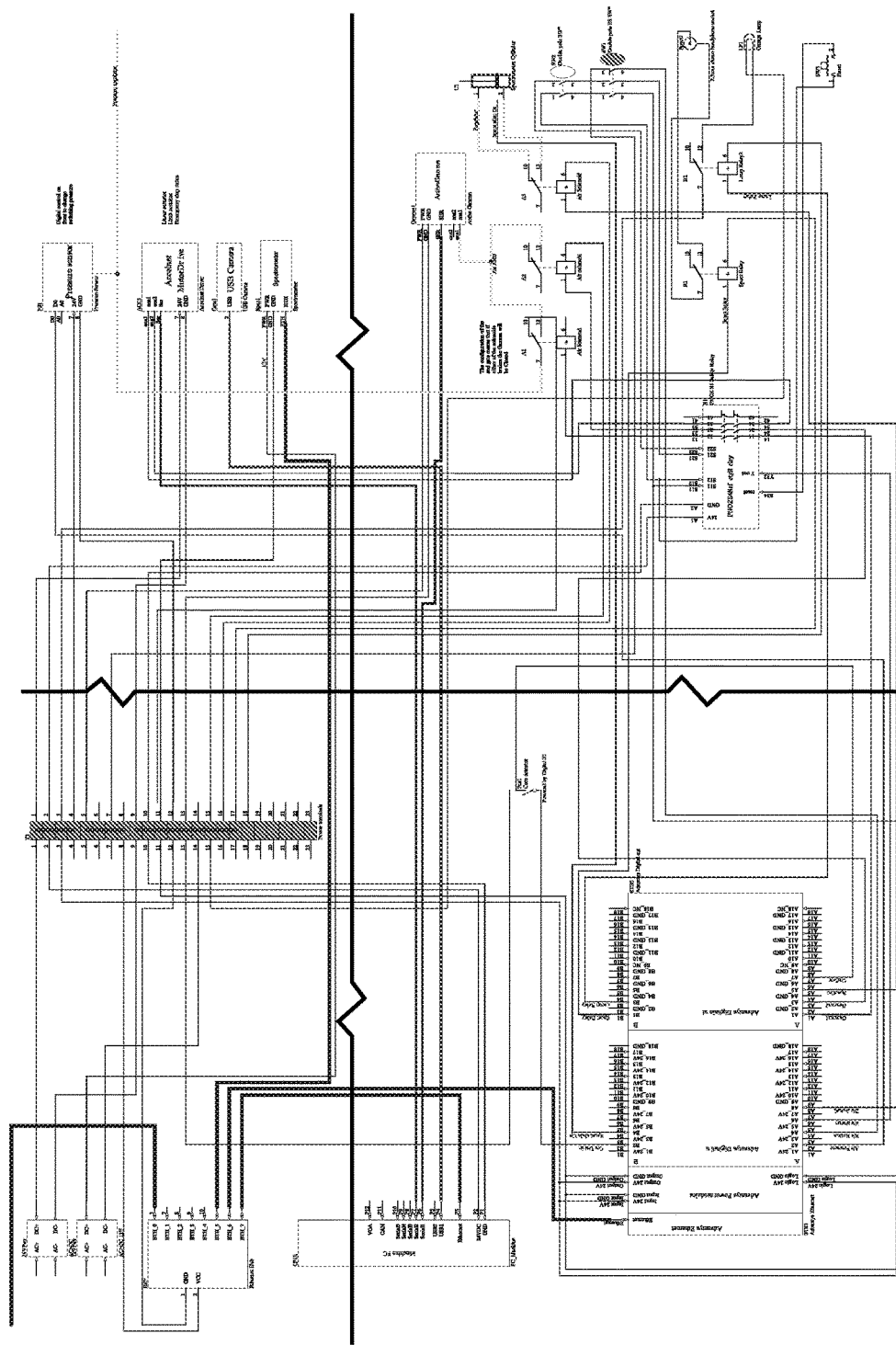

SOIL CONDITION ANALYSIS SYSTEM AND PROCESS

This application is a National Stage Application of PCT/AU2016/050500, filed 15 Jun. 2016, which claims benefit of Serial No. 2015902264, filed 15 Jun. 2015 in Australia and which applications are incorporated herein by reference. To the extent appropriate, a claim of priority is made to each of the above disclosed applications.

TECHNICAL FIELD

The present invention relates to a soil condition analysis system and process, and in particular to a system and process that measure soil properties and use mathematical and statistical methods to derive the condition of soil as a function of depth.

BACKGROUND

Information on the condition of soils is needed to address environmental concerns over food production, water and energy securities, land degradation, and climate change. It is also needed for the long-term provision of ecosystem function and ecosystem services, which are important for human well-being and economic development. However, although soils are central to these concerns, not enough is known about their properties, composition, functions, diversity and distributions. The main reason is that soil science has been constrained by the inconvenience and high costs of existing soil measurement methods, including outdated and on occasions imprecise laboratory techniques, and the need to measure at depth down to the root zone or deeper.

It is desired to provide a soil condition analysis system and process that alleviate one or more difficulties of the prior art, or to at least provide a useful alternative.

SUMMARY

In accordance with some embodiments of the present invention, there is provided a soil condition analysis system, including:
- a support platform to support an elongate soil core extracted from the Earth;
- a plurality of soil sensing components configured to measure corresponding characteristics of a soil core supported on the support platform, including a camera to image the soil core, an optical spectrometer to measure light from the soil core at near-infrared and/or mid-infrared wavelengths, and a gamma ray attenuation component to measure attenuation of gamma-rays transmitted through the soil core;
- one or more data acquisition components in communication with the soil sensing components and configured to generate measurement data representing the measured characteristics from the soil sensing components; and
- a data processing component configured to process the measurement data to generate soil property data representing corresponding soil properties of the elongate soil core as a function of depth, based on spectroscopic models representing relationships between the soil properties and the measured characteristics;
- wherein at least one of the support platform and the plurality of soil sensing components is mounted on a computer-controlled translation stage to enable the soil sensing components to automatically measure the corresponding characteristics of the soil core at mutually spaced locations along a longitudinal axis of the elongate soil core;
- wherein the data processing component is configured to generate estimates of the bulk density of the soil core as a function of depth from the measured attenuation of gamma rays through the soil core and the measured water content of the soil core by compensating for the absorption of the gamma rays by the water content of the soil core to generate estimates of the bulk density of the soil core without the water content;
- wherein the water content of the soil core is determined from spectroscopic modelling of visible-near infrared spectra measured from the soil core.

In some embodiments, the soil sensing components include a long wave infrared (LWIR) camera.

In some embodiments, the soil sensing components include an x-ray sensor component to measure x-ray fluorescence of the soil or x-ray transmission through the soil core.

In some embodiments, the soil sensing components include at least one of a microwave soil water sensing component and a laser induced breakdown spectroscopy (LIBS) sensing component.

In some embodiments, the soil condition analysis system includes a display component to display, during data acquisition, a visual image of at least a corresponding portion of the soil core together with measurement data being acquired from at least one other of the soil sensing components.

In some embodiments, the soil properties includes at least five of: soil organic carbon, organic carbon composition (particulate, humic, and resistant carbon), bulk density, soil carbon stocks, soil water, available water capacity, clay content, iron mineralogies, soil colour, clay mineralogies, cation exchange capacity, total nitrogen, and pH.

In some embodiments, the spectroscopic models are generated by machine learning applied to a soil spectral library of previously measured soil spectra and corresponding soil properties.

In some embodiments, the spectroscopic models are generated by analysing a representative subset of a plurality of soil cores taken from a common geographic region to be analysed to determine the soil properties of the subset of soil cores by laboratory analysis, and associating the determined soil properties with corresponding spectra from the subset of soil cores; using the relationships between the determined soil properties and corresponding spectra to customise a soil spectral library of previously measured soil spectra and corresponding soil properties by removing those members of the soil spectral library that are least representative of the subset of soil cores and adding the determined soil properties and corresponding spectra of the subset of soil cores to the remaining members of the soil spectral library to provide a soil spectral library customised to the common geographic region; and generating the spectroscopic models from the customised soil spectral library.

In some embodiments, the members of the soil spectral library are removed by iteratively removing corresponding members of the soil spectral library that are least representative of the subset of soil cores as determined by a corresponding partial least squares regression performed in each iteration. In some embodiments, a fixed proportion of the remaining number of members of the soil library are removed in each iteration.

In some embodiments, the representative subset of soil cores is selected by the Kennard-Stone method.

In some embodiments, the support platform, soil analysis components, and data acquisition components are mounted on a trailer such that the system can be transported to a site where soil core are to be extracted for measurement by the system.

In accordance with some embodiments of the present invention, there is provided using a soil condition analysis system to generate measurement data representing measured characteristics of an elongate soil core at mutually spaced locations along a longitudinal axis of the elongate soil core by controlling a computer-controlled translation stage to automatically translate at least one of a support platform on which the soil core is supported and a plurality of soil sensing components configured to measure corresponding characteristics of the soil core, the plurality of soil sensing components including a camera to image the soil core, an optical spectrometer to measure light from the soil core at near-infrared and/or mid-infrared wavelengths, and a gamma ray attenuation component to measure attenuation of gamma-rays transmitted through the soil core;

processing the measurement data to generate soil property data representing corresponding soil properties of the elongate soil core as a function of depth, based on spectroscopic models representing relationships between the soil properties and the measured characteristics, including determining water content of the soil core from spectroscopic modelling of visible-near infrared spectra measured from the soil core; and;

generating estimates of the bulk density of the soil core from the measured attenuation of gamma rays through the soil core and the determined water content of the soil core by compensating for the absorption of the gamma rays by the water content of the soil core to generate estimates of the bulk density of the soil core without the water content.

In some embodiments, the process includes applying machine learning to a spectral library of previously measured soil spectra and corresponding soil properties to generate the spectroscopic models.

In some embodiments, the spectroscopic models are generated by analysing a representative subset of a plurality of soil cores taken from a common geographic region to be analysed to determine the soil properties of the subset of soil cores by laboratory analysis, and associating the determined soil properties with corresponding spectra from the subset of soil cores; using the relationships between the determined soil properties and corresponding spectra to customise a soil spectral library of previously measured soil spectra and corresponding soil properties by removing those members of the soil spectral library that are least representative of the subset of soil cores and adding the determined soil properties and corresponding spectra of the subset of soil cores to the remaining members of the soil spectral library to provide a soil spectral library customised to the common geographic region; and generating the spectroscopic models from the customised soil spectral library.

In some embodiments, the customising of the soil library includes iteratively removing members of the soil library that are least representative of the subset of soil cores as determined by a partial least squares regression.

In some embodiments, a fixed proportion of the remaining number of members of the soil library are removed in each iteration.

In some embodiments, the representative subset of soil cores is selected by the Kennard-Stone method.

In some embodiments, the soil properties includes at least five of: soil organic carbon, organic carbon composition (particulate, humic and resistant organic carbon), bulk density, soil carbon stocks, soil water, available water capacity, clay content, total nitrogen, iron mineralogies, clay mineralogies, soil colour, cation exchange capacity, and pH.

In accordance with some embodiments of the present invention, there is provided at least one computer-readable storage medium having stored thereon executable instructions that, when executed by at least one processor of a data processing system, cause the at least one processor to execute any one of the above processes.

Also described herein is a soil measurement system, including:
- a support platform to support an elongate soil core extracted from the Earth;
- a plurality of soil analysis components configured to measure respective properties of a soil core on the support platform;
- data acquisition components configured to acquire, from the soil analysis components, measurement data representing the soil properties measured by the soil analysis components;
- wherein at least one of the support platform and the plurality of soil analysis components is mounted on a computer-controlled translation stage to enable the soil analysis components to automatically measure the properties of the soil core at respective locations along a longitudinal axis of the elongate soil core.

The soil analysis components may include a camera to image the soil core at visible wavelengths, a camera to image the soil core at thermal wavelengths, an optical spectrometer to measure light from the soil core at near-infrared or mid-infrared wavelengths, and a gamma ray attenuation component to measure attenuation of gamma-rays transmitted through the soil core.

The soil measurement system may include a data processing component configured to generate measurements of the bulk density of the soil core by measuring the attenuation of gamma rays through the soil core and the water content of the soil core, and compensating for the absorption of the gamma rays by the water content of the soil core to generate estimates the bulk density of the soil core without the water content.

Also described herein is a soil measurement process, including:
- receiving sample gamma attenuation data representing the measured attenuation of gamma rays through a soil sample;
- receiving optical spectral data representing measured visible-near infrared optical spectra from the soil sample;
- processing the optical spectral data to generate water content data representing water content of the soil sample;
- processing the sample gamma attenuation data and the water content data to generate soil gamma attenuation data representing the attenuation of gamma rays through the soil sample without the water content; and
- processing the soil gamma attenuation data to generate bulk density data representing the bulk density of the soil sample.

The soil measurement process may include processing the optical spectral data and the sample gamma attenuation data to generate at least five soil attribute depth functions to determine soil condition data representing estimates of at least five of: soil organic carbon, organic carbon composition (particulate, humic and resistant organic carbon), bulk density, soil carbon stocks, soil water, clay content, total nitrogen, iron mineralogies, clay mineralogies, soil colour, cation exchange capacity, and pH.

BRIEF DESCRIPTION OF THE DRAWINGS

Some embodiments of the present invention are hereinafter described, by way of example only, with reference to the accompanying drawings, wherein:

FIG. 4 is further depicted in magnified form by FIGS. 4A, 4B, 4C, and 4D.

DETAILED DESCRIPTION

Figure 1:
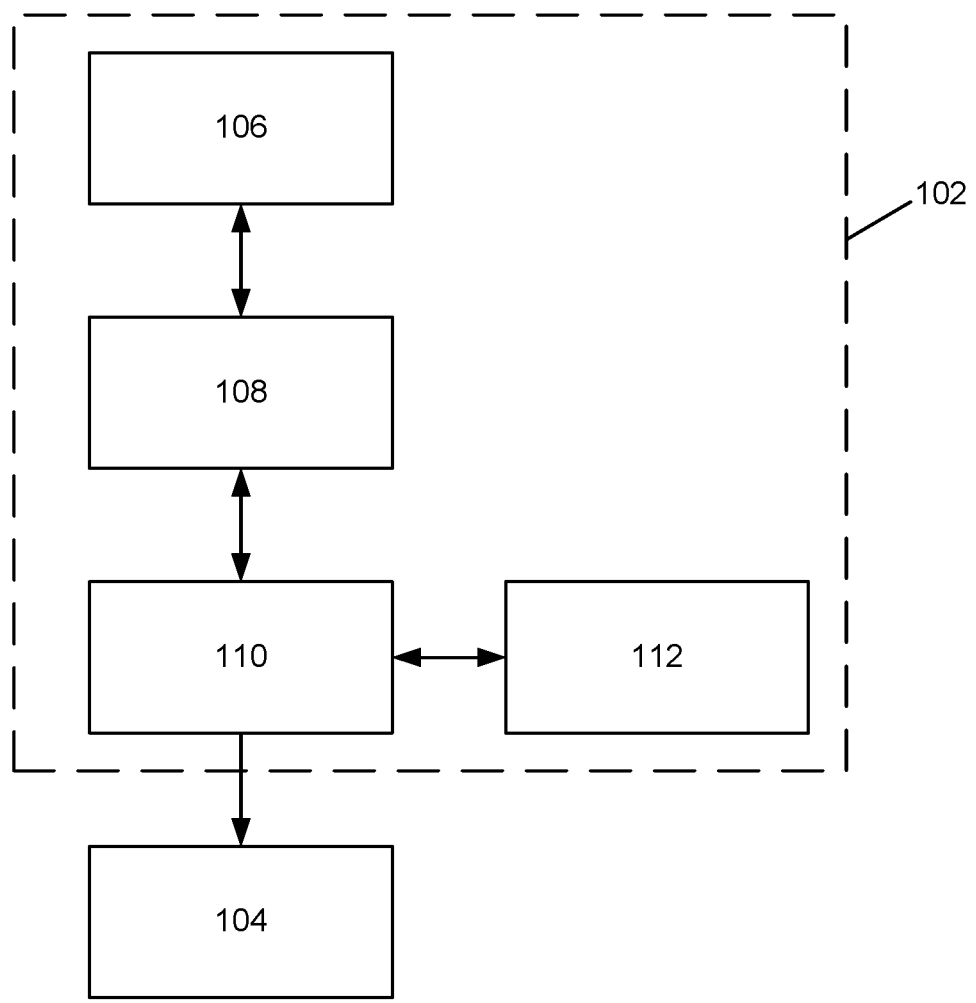
FIG. 1 is a block diagram of a soil condition analysis system in accordance with an embodiment of the present invention.
Figure 2:
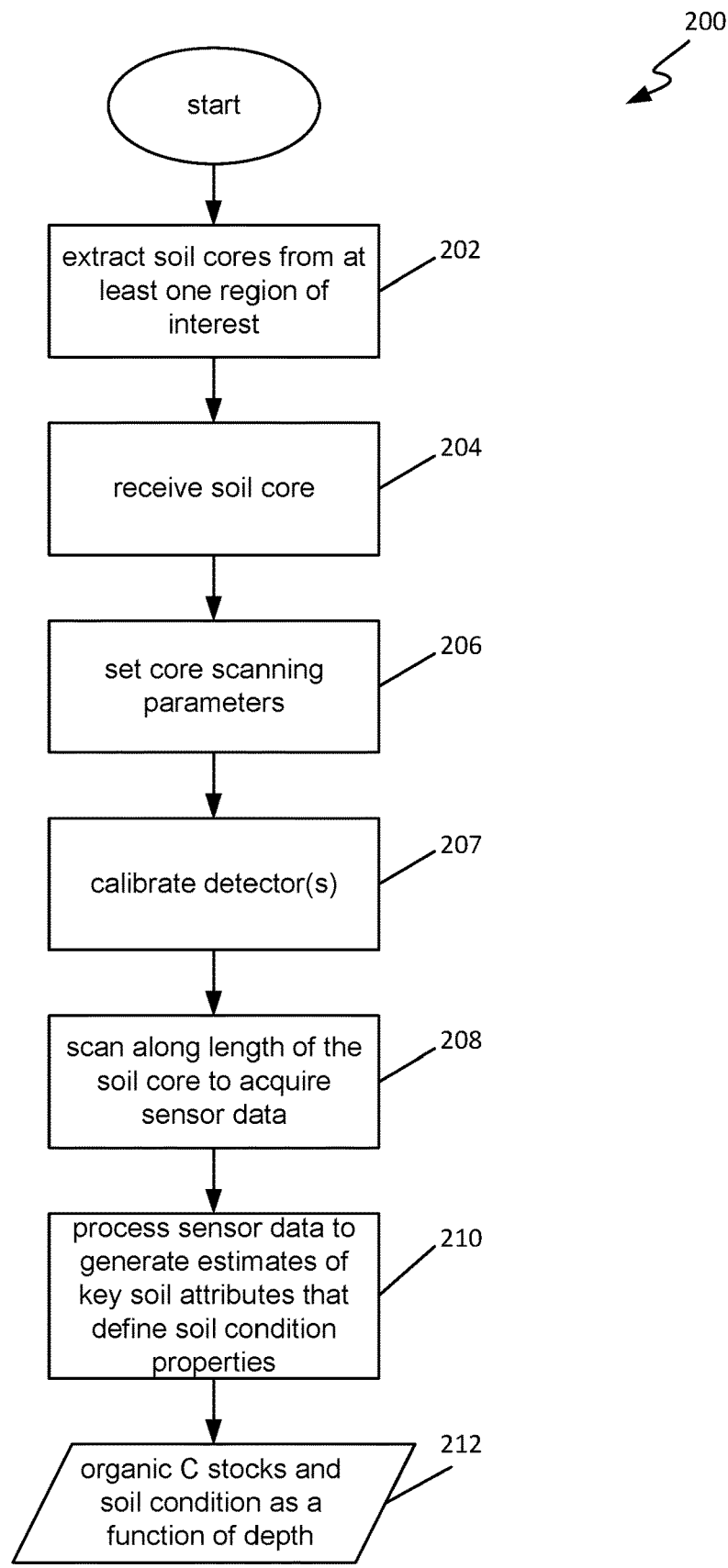
FIG. 2 is a flow diagram of a soil condition analysis process in accordance with an embodiment of the present invention.
Figure 3C:
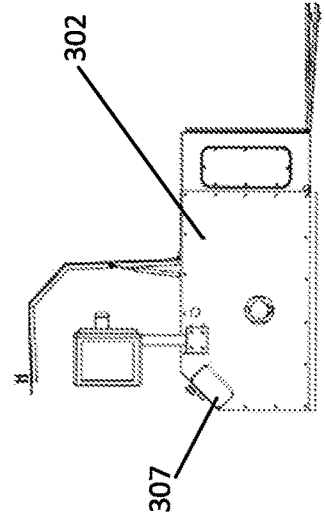
FIGS. 3A-3E are diagrams showing plan, front, side and perspective views of a soil core multisensory platform of the system.
Figure 3A:
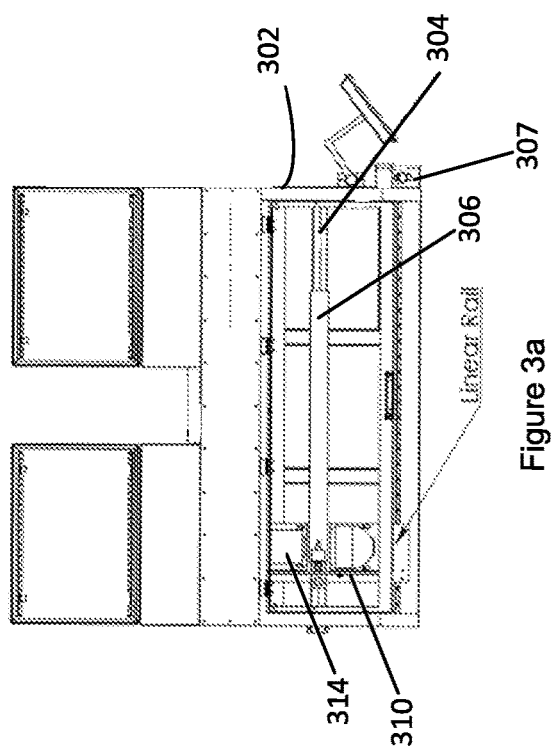
Figure 3B:
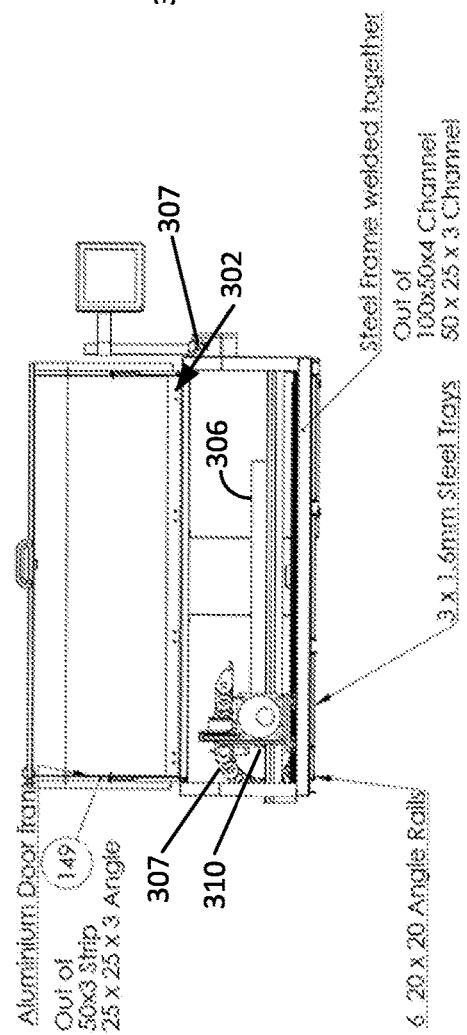
Figure 3E:
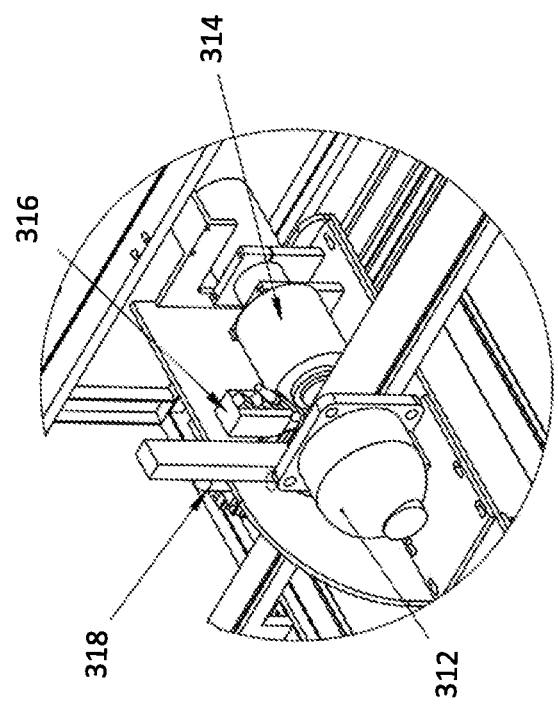
Figure 3D:
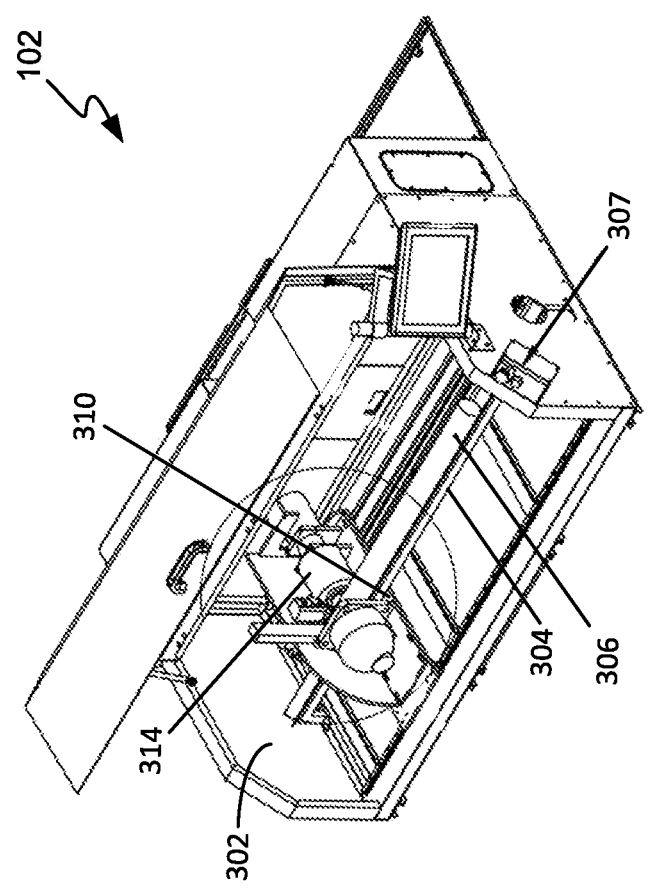
Figure 4A:
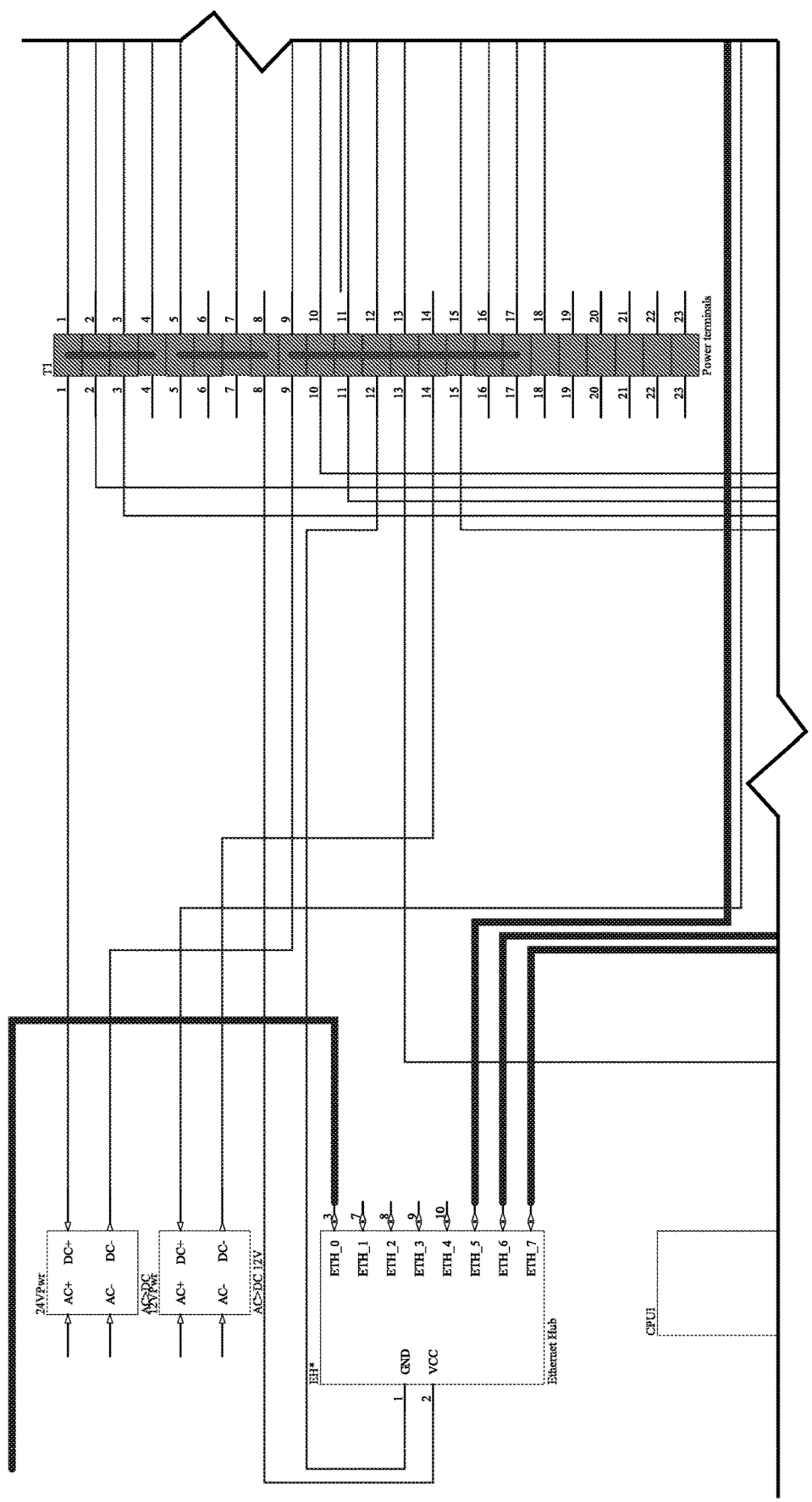
FIG. 4 is a diagrams showing the components and connections of a power and multisensory measurement control sub-system of the soil core multisensory platform of FIGS. 3A-3E. For clarity.
Figure 4B:
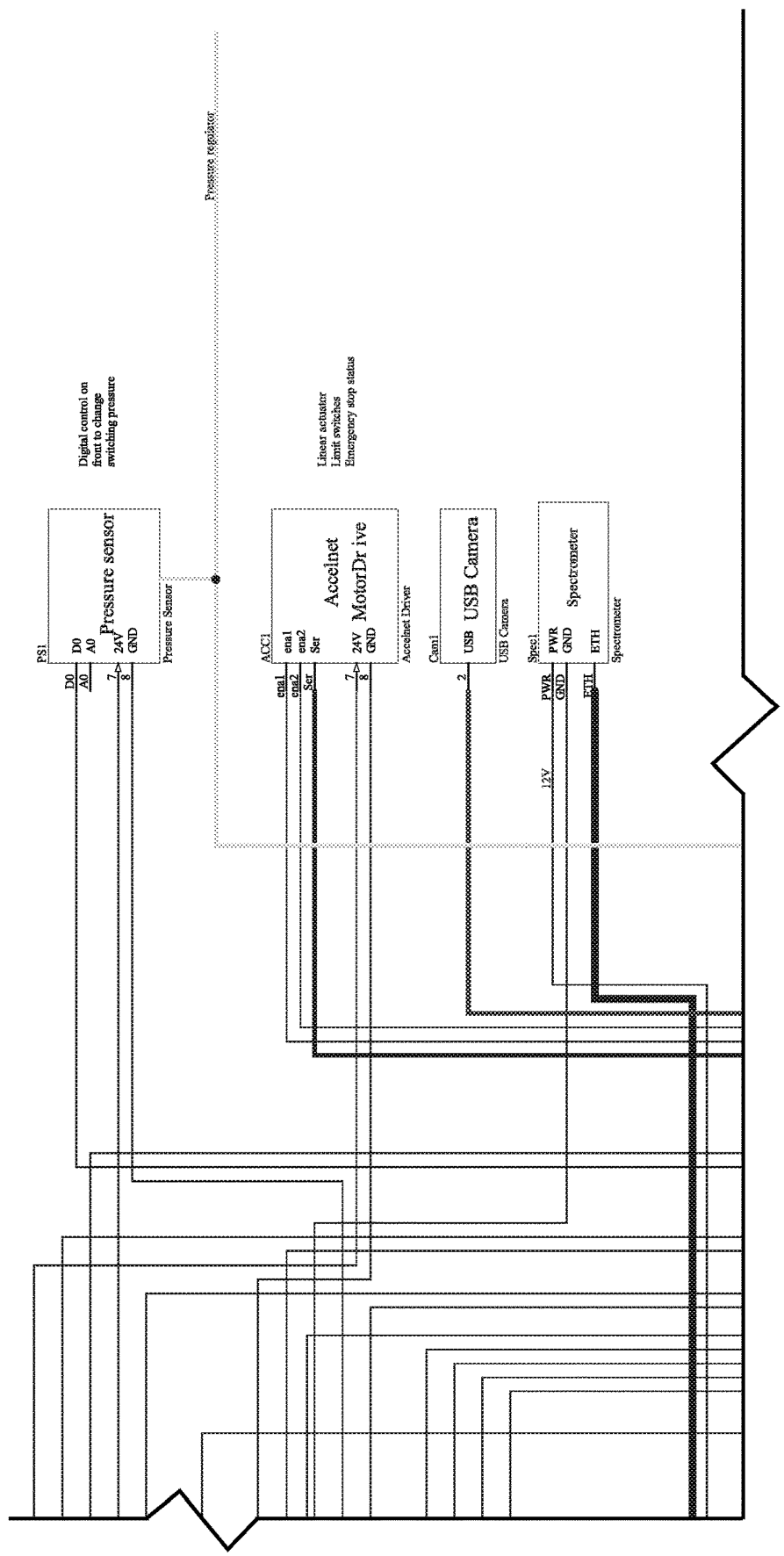
Figure 4C:
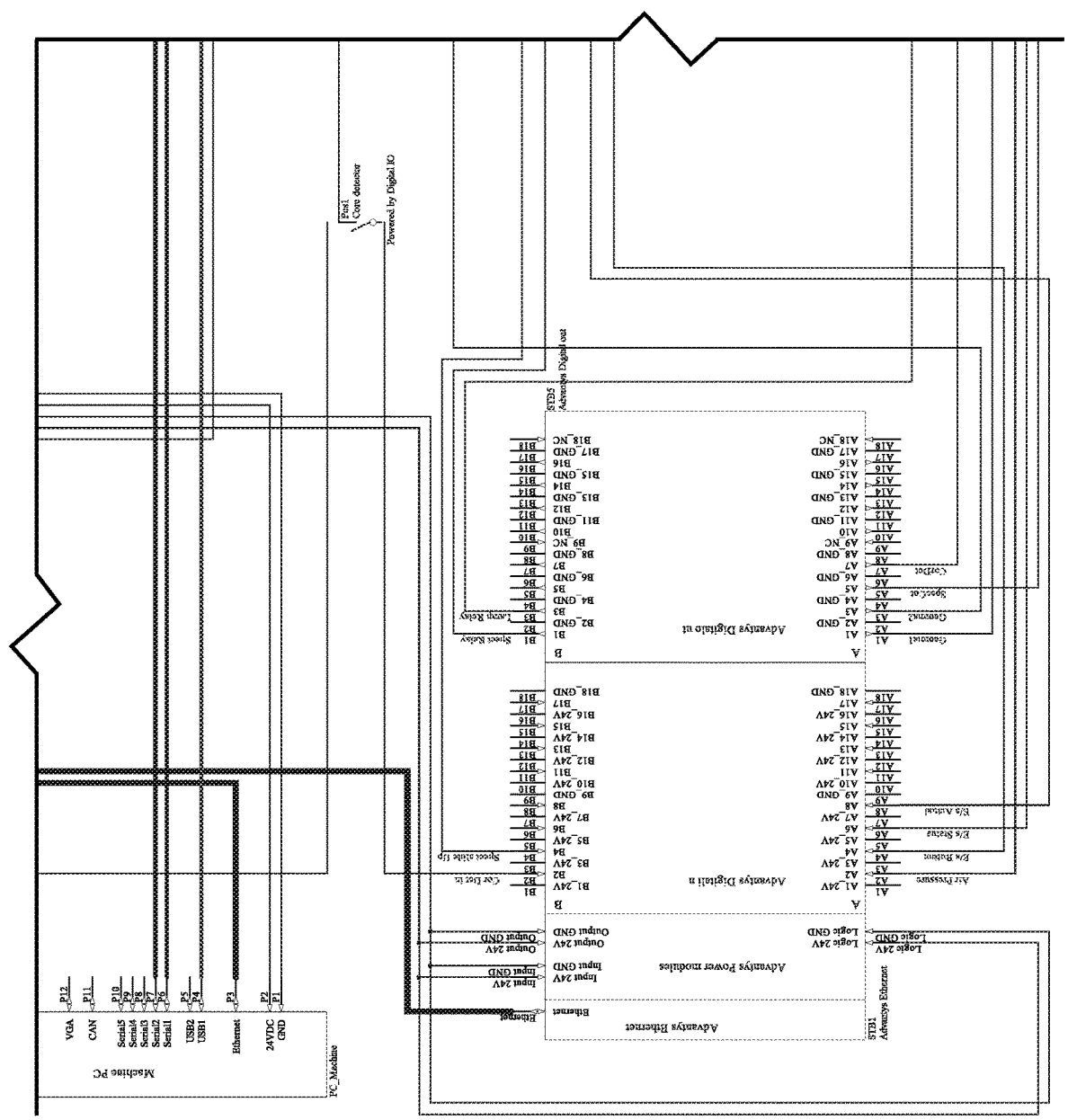
Figure 4D:
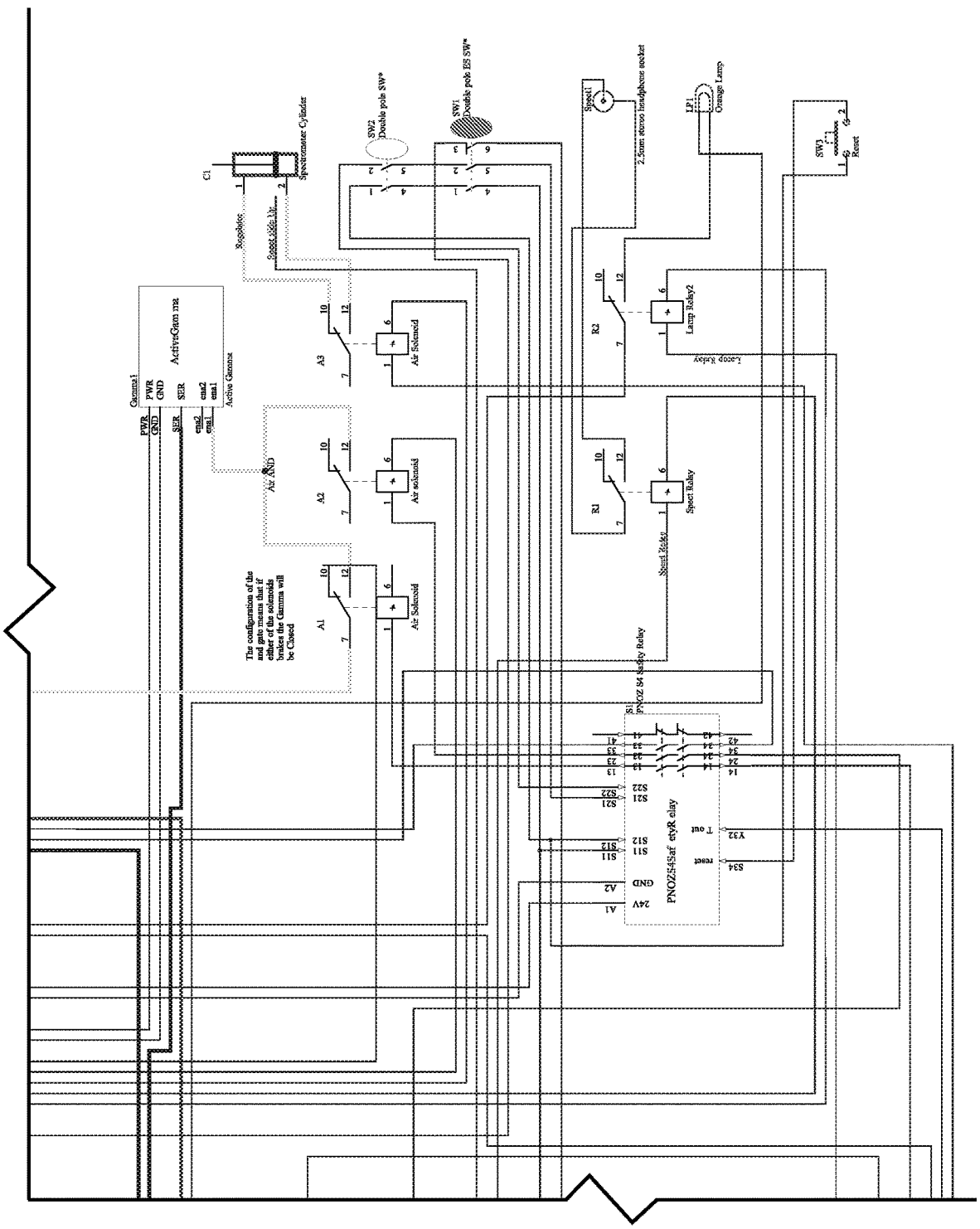

As shown in the embodiment of FIG. 1, a soil condition analysis system 100 includes a soil core measuring component 102 and a soil data analysis component 104. The system 100 executes a soil condition analysis process, as shown in FIG. 2, that measures a range of soil characteristics as a function of depth along the length of a soil core, and processes the resulting measurement data to determine soil property depth functions to assess soil condition. The soil properties include at least five of soil organic carbon content, organic carbon composition (particulate, humic and resistant carbon), bulk density, soil carbon stocks, soil water, available water capacity, clay content, total nitrogen, iron and clay mineralogies, soil colour, cation exchange capacity, and pH.

The soil core measuring component 102 includes sensing and analysis hardware components 106, a power (electrical and pneumatic), safety interlock, control and data acquisition sub system 108, and a control computer 110 coupled to a touchscreen display device 112. There is a separate PILZ (https://www.pilz.com/en-AU/) safety system which runs in parallel with the main Computer touch screen. In particular, we have a PILZ safety relay that overseas the safety aspects of the system.

As shown in FIGS. 3A to 3E, the sensing and analysis hardware components 106 include an elongate housing 302 having an elongate support bed or platform 304 to support a soil core 306 in a generally horizontal orientation. In the described embodiments, the support platform 304 can accommodate soil cores 306 having lengths up to 1.5 m and diameters in the range from about 50 mm to 85 mm; however, it will be apparent to those skilled in the art that in other embodiments the system 100 can be configured to accommodate soil cores having essentially any practical dimensions.

As shown in FIG. 4, the operator is protected using a safety interlock relay system (Pilz, PNOZ S4). For clarity, FIG. 4 is further depicted in magnified form by FIGS. 4A, 4B, 4C, and 4D. The safety interlocks include an e-stop switch 307, a multisensor measurement platform enable button to reset the safety interlock and a sensor to detect closure of the multisensor platform door. The interlocks disable operation of the linear translation stage 310 (linear actuator) via the servo drive and pneumatic components related to operator safety e.g. where the sensor components 308 include an active gamma ray attenuation sensor, the pneumatically operated protective shutter of the gamma ray source is not opened when interlocks are active.

Soil analysis components 308 are mounted to a linear translation stage 310 that allows the analysis components 308 to be moved to any desired location along the entire length of the soil core 306 by way of a linear actuator (partially visible in the isometric drawing in FIG. 3), with the associated cables supported by a cable train. The linear actuator is under control of the computer 110 via a servo drive (Copely Controls—Accelnet) with encoder feedback. Typically, this is used to automatically translate the stage 310 along the entire length of the soil core 306 in a continuous or stepwise manner, acquiring data from the analysis components 308 while the stage 310 is moving or is stationary between successive translation steps, in order to acquire data at many locations along the length of the soil core 306. Optical proximity sensors (not shown) are mounted on the linear translation stage 310 to determine the absolute position and length of the soil core 306 on the support platform 304.

The soil analysis components 308 include different types of analysis components in order to acquire respective types of analysis data and thereby more comprehensively characterise the composition and structure of the soil core 306. In the described embodiments, the soil analysis components 308 include at least an active gamma ray attenuation sensor (an LB444 sensor from Berthold Technologies GmbH, Germany), a visible to near-infrared (vis-NIR) optical spectrometer and contact Probe (both from PANalytical, formerly Analytical Spectral Devices Inc. (ASDI), Boulder, Colo. USA), and a digital camera (Logitech C920). In some embodiments, the system 100 also includes one or more of an X-Ray Fluorescence (XRF) analysis component for soil elemental analysis, an X-Ray transmission (attenutation) sensor, a mid-infrared (MIR) spectrometer, a microwave soil water analysis component, and/or a laser induced breakdown spectroscopy (LIBS) analysis component.

Figure 17:
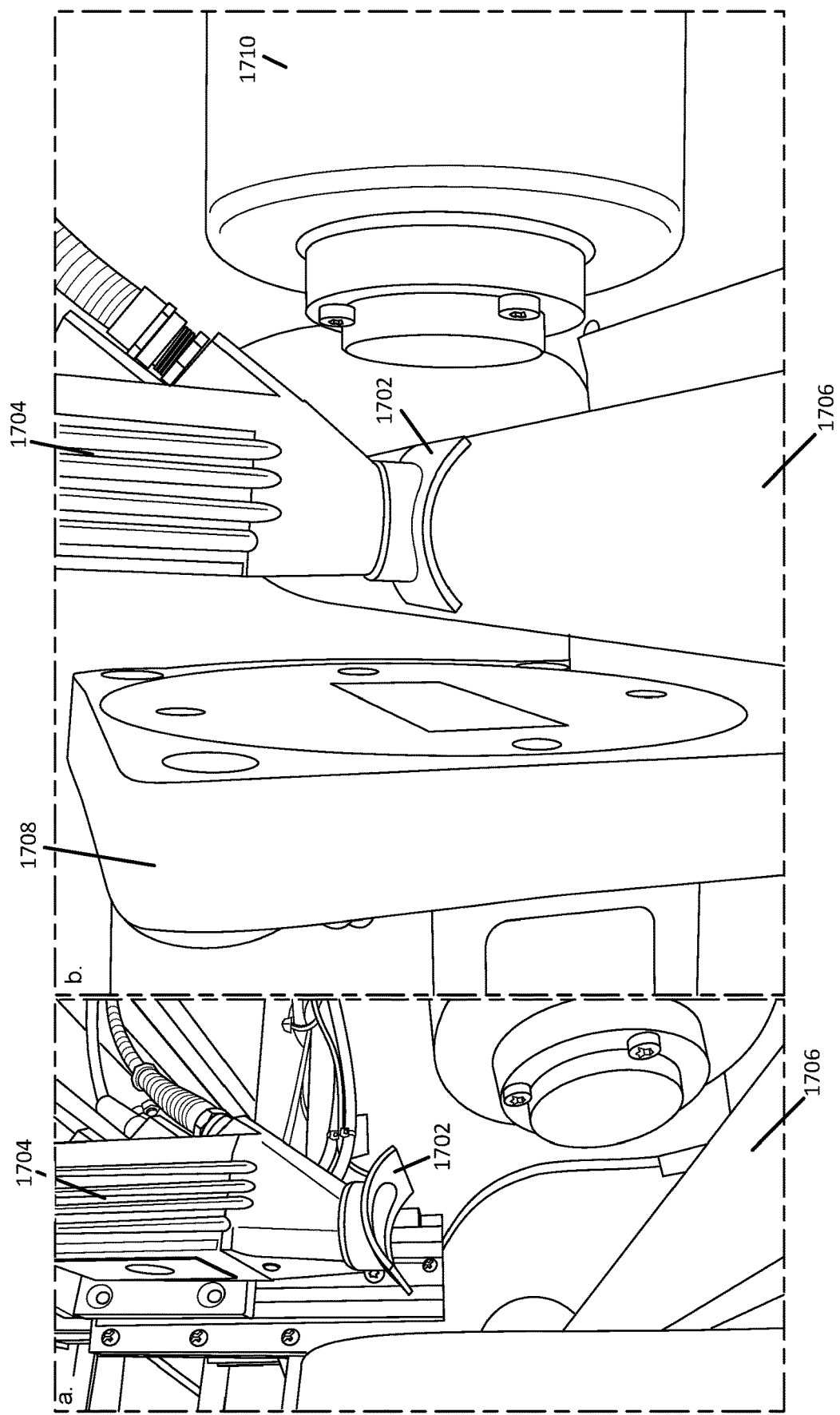
FIG. 17 is a pair of photographic images showing a contact probe soil core attachment of the system moving from a raised position (left-hand image) to being in direct contact with (right-hand image) an elongate soil core disposed between a gamma radiation source and a gamma ray detector of the system.

The contact probe illuminates a spot of diameter 10 mm with high intensity halogen light bulb (2901±10K) to reduce errors arising from stray light entering the spectrometer. As shown in FIG. 17, the system 102 includes an attachment 1702 for the contact probe 1704 that prevents the window of the probe 1704 from coming into contact with the soil core 1706 and for additional optical shielding. The attachment which can be made manually with PVC or 3D printed from Nylon, includes a part-cylindrical shell whose inner curvature matches the outer curvature of the soil core 1706. In use, the probe 1704 with attachment 1702 drops down pneumatically until it comes into contact with the soil core 1706 so that the contact probe 1704 is positioned close to the surface of the soil core 1706.

In the described embodiments, the gamma ray sensor is an LB444 sensor from Berthold Technologies GmbH, Germany, and is used to make gamma-ray attenuation measurements of soil bulk density, as described below. The sensor includes a shielded $^{137}$Cs gamma ray source 1708 having an activity of 185 MBq and emitting gamma rays with an energy of 0.662 MeV. The source 1708 is equipped with a pneumatically operated shutter that is controlled with the multisensor platform's safety interlock. The detector 1710 is an LB5441-01 (Berthold Technologies 135 GmBH, Germany) with an uncollimated NaI scintillation crystal of 25 mm diameter and 25 mm length. As shown in FIG. 17, the source 1708 and detector 1710 are positioned on opposite sides of a soil core 1706 to enable measurements of the attenuation of gamma rays passing through the core 1706 along paths traversing thin circular disk portions of each cylindrical soil core.

Figure 16:
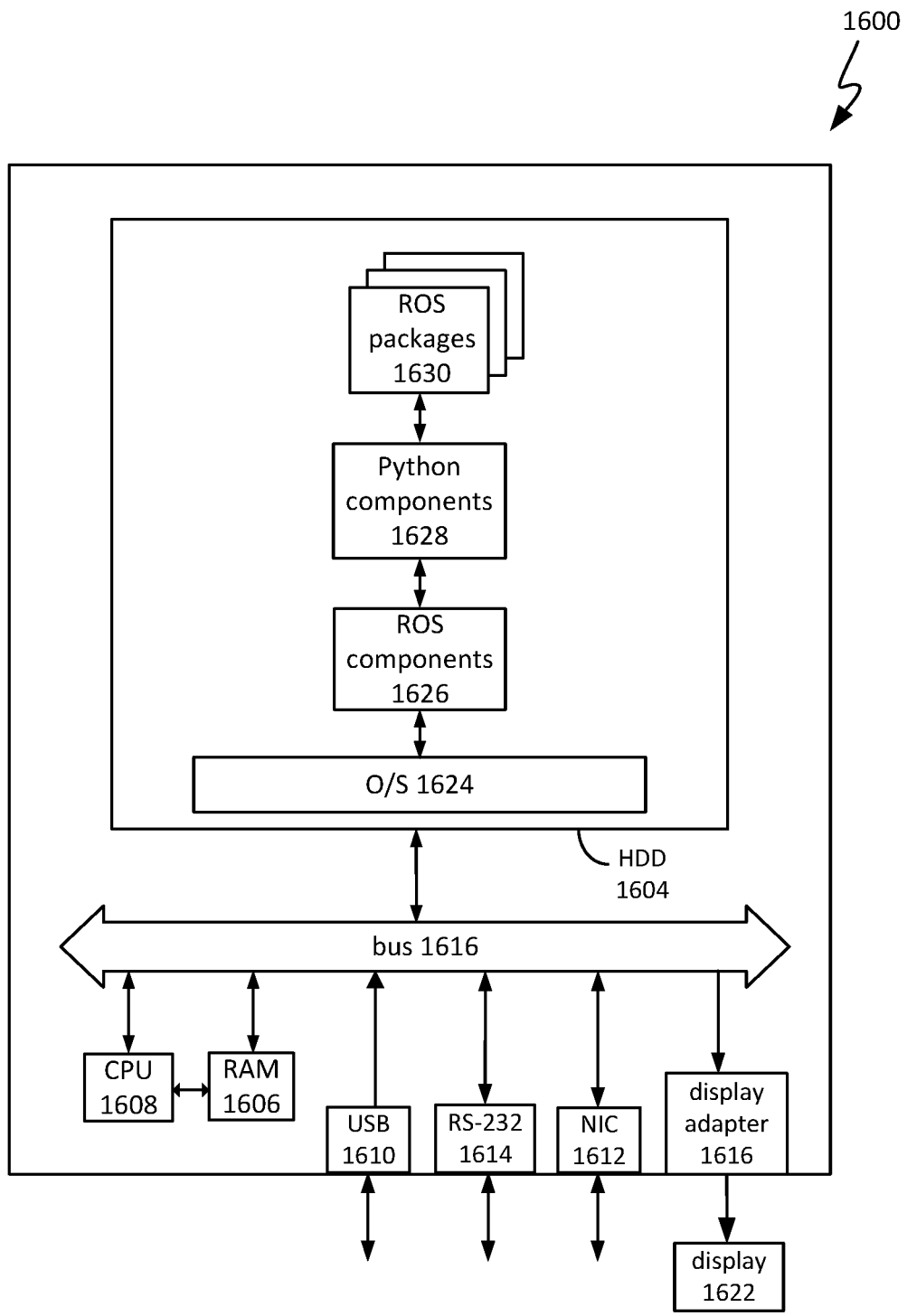
FIG. 16 is a block diagram of a control computer of the system.

In the described embodiments, the control computer 110 is a computer system such as an Intel IA-64 based computer system, as shown in FIG. 16, and the processes executed by the system 100 are implemented as programming instructions of software modules 1602 stored on non-volatile (e.g., hard disk or solid-state drive) storage 1604 associated with the computer system, as shown in FIG. 3. However, it will be apparent that in other embodiments, at least portions of the processes could alternatively be implemented as one or more dedicated hardware components, such as application-specific integrated circuits (ASICs) and/or as configuration data of one or more field programmable gate arrays (FPGAs), for example. It will also be apparent to those skilled in the art that in other embodiments the various components of the control computer 110 may be distributed and/or combined in a variety of alternative ways other than those described herein, and/or at a number of alternative locations.

The control computer 110 includes standard computer components, including random access memory (RAM) 1606, at least one processor 1608, and external interfaces 1610, 1612, 1614, all interconnected by at least one bus 1616. The external interfaces include universal serial bus (USB) interfaces 1610, a network interface connector (NIC) 1612 which provides Ethernet connectivity, an RS-232 interface 1614, and a display adapter 1616, which is connected to a display device such as a touchscreen LCD panel display 1622.

The control computer 110 also includes a number of standard software modules 1626 to 1630, including an operating system 1624 such as Linux, robotic operating system (ROS) components 1626, available from the ROS web site at http://www.ros.org, and Python programming language support 1628, available from http://www.python.org. As known to those skilled in the art, the ROS software framework enables robotic control applications to be implemented as a distributed network of executable components referred to as "nodes" that communicate with one another via IP-based publish and subscribe messaging. In the described embodiments, the processes executed by the system 100 are implemented as ROS packages 1630 written in Python and C++ to implement respective ROS nodes 502 to 514, as described below. Each node can subscribe to one or more "topics" and then receive messages published to those topics by other nodes.

In the system 100, each of the soil analysis components 308 interfaces with a corresponding ROS software node which publishes data into the publish/subscribe network, and a controller node 512 manages all the data collection. Whilst a measurement is running, the controller node builds an in-memory data structure of all samples and then saves this data to disk in open format YAML files for processing by other applications.

Figure 5:
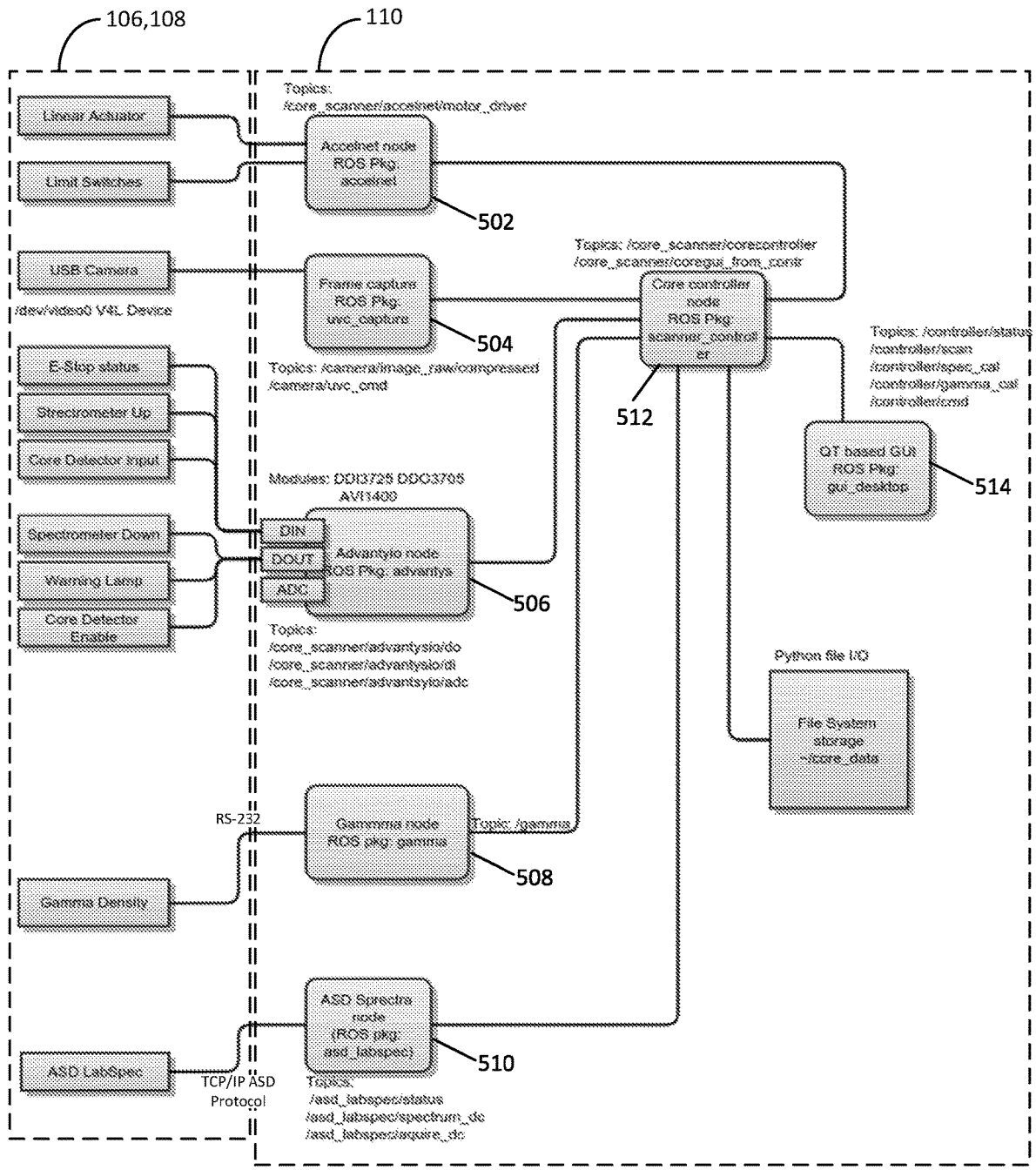
FIG. 5 is a block diagram showing the relationships between the hardware components of the soil core multisensor platform and software components of the system.

In the embodiment of FIG. 5, the ROS architecture of the system 100 includes the following seven nodes:
(i) accelnet node 502 (to control the linear translation stage);
(ii) uvc_capture node 504 (digital image capture from USB camera);
(iii) advantys node 506 (ADC and digital i/o);
(iv) gamma node 508 (gamma density sensor);
(v) asd_labspec node 510 (vis-NIR spectrometer);
(vi) scanner_controller node 512 (central controller, data management, sampling); and
(vii) gui_desktop node 514 (user interface, visualisation).

Figure 6:
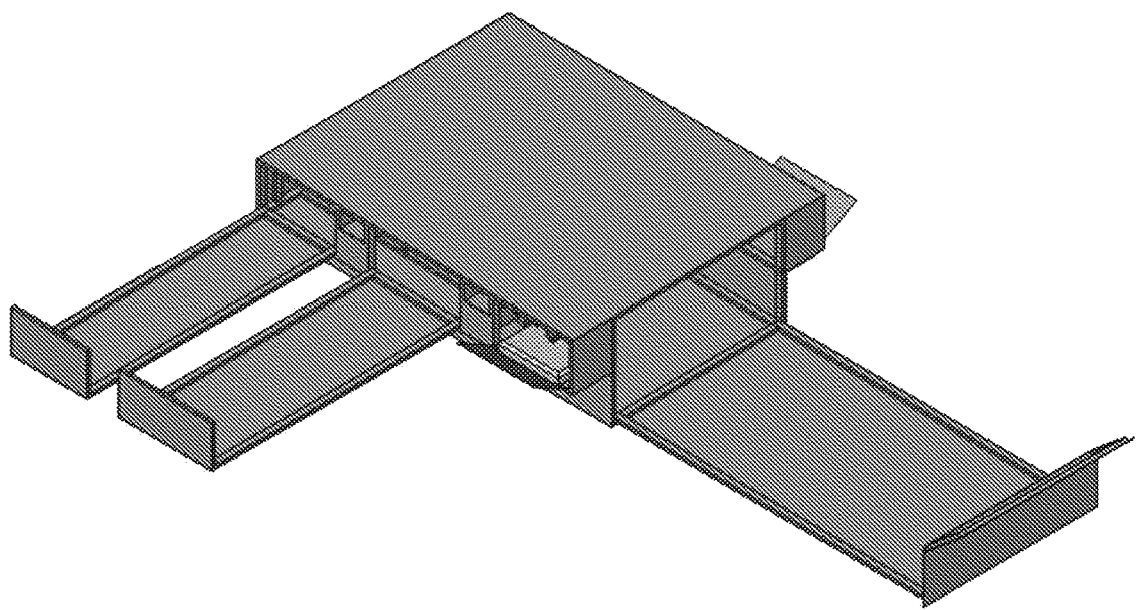
FIGS. 6 and 7 are CAD drawings of a base component of the soil core multisensor platform with its drawers open and closed, respectively.
Figure 7:
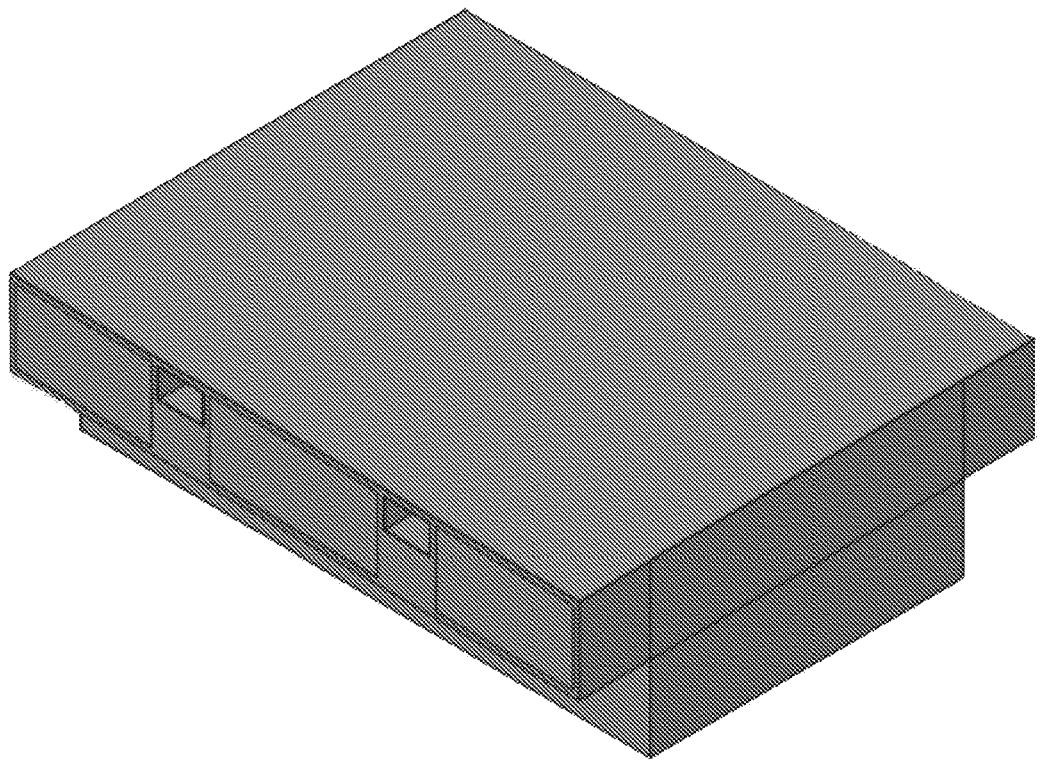
Figure 8:
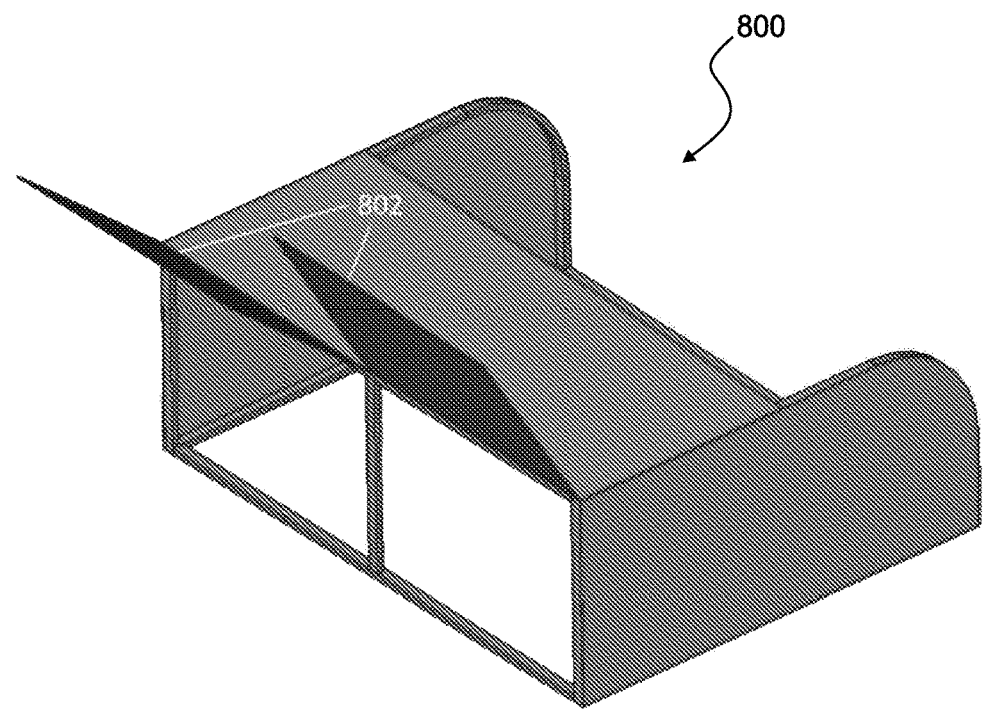
FIG. 8 is a CAD drawing of a hood component of the soil core multisensor platform, shown from the rear with access flaps open.
Figure 9:
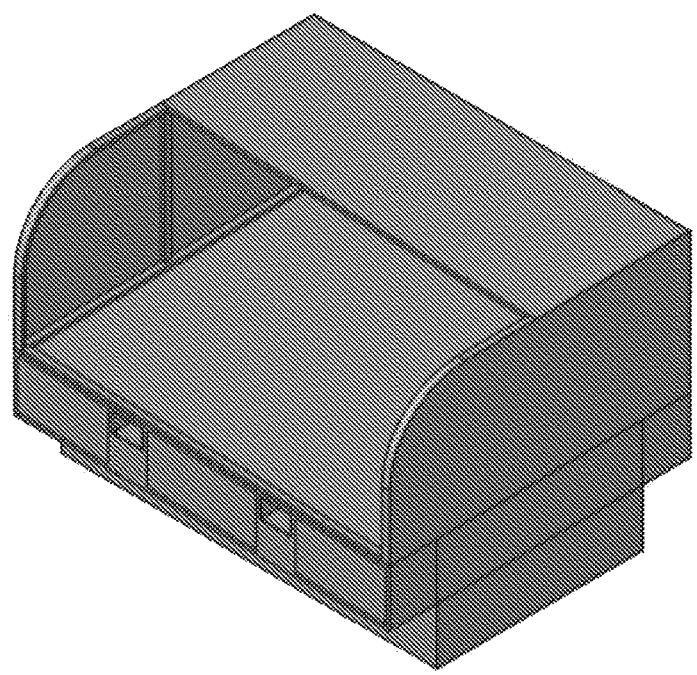
FIG. 9 is a CAD drawing of the hood component mounted to the base component to form an enclosure for the soil core multisensor platform.

In the described embodiments, the soil core measurement system 100 is mounted within a protective enclosure, as shown in FIGS. 3 and 6 to 10. The enclosure includes a base component 600, as shown in FIGS. 6 and 7, onto which the soil measurement system 100 is mounted via rubber vibration isolation components. The base component 600 includes storage compartments in the form of sliding drawers, for storing core samples and general-purpose storage, including a storage compartment for a generator and compressor: Generator Honda EP2200CX and compressor Maxus CHWX1001. A hood component 800, as shown in FIG. 8, sits on top of the base component 600, as shown in FIG. 9, in order to protect the system 100 from the elements. The hood component 800 includes rear flaps 802 that are operable to allow access to the power and multisensor platform control sub-system 108.

Figure 10:
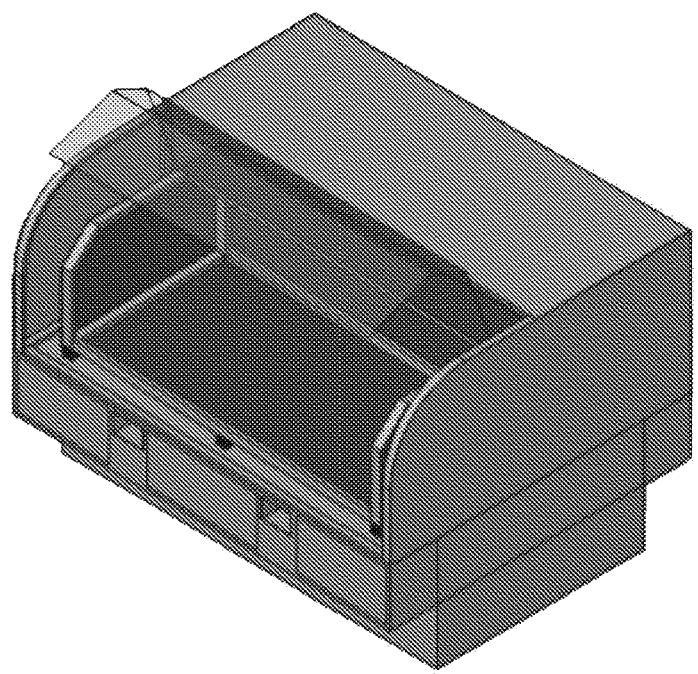
FIG. 10 is a CAD drawing of the soil core multisensor platform installed within the enclosure of FIG. 9.

FIG. 10 shows the elongate housing 302 of the sensing and analysis hardware components 106 installed within the enclosure, and a transparent access door of the enclosure in an open position in order to allow access to the soil core and soil analysis components 308.

Figure 11:
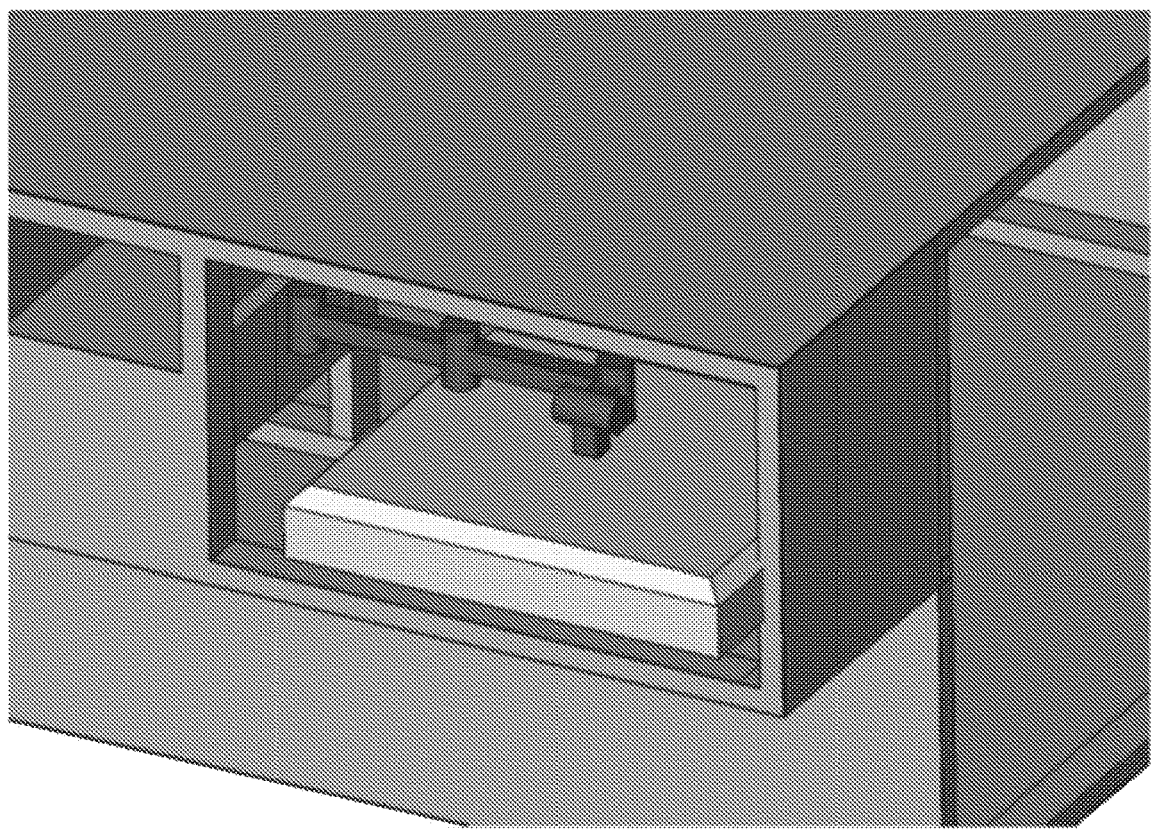
FIG. 11 is a CAD drawing showing a computer mounting platform within a front right-hand draw of the base of the enclosure.

FIG. 11 is a close-up of the front right-hand storage compartment of the base component 600, showing an optional articulated arm to which the touchscreen display device 112 can be mounted in some embodiments.

Figure 24:
FIG. 24 is a set of three photographs showing the soil core measuring component mounted on a trailer and being used on site to measure characteristics of soil cores.

In the described embodiments, the enclosure is mounted on a wheeled trailer as shown in FIG. 24, which allows the soil core multisensor platform measurement component 102 to be towed by a vehicle to essentially any desired location that can be accessed by a vehicle. In particular, the resulting portability of the soil core multisensor platform measurement component 102 allows it to be transported to locations or sites where soil cores are to be extracted, allowing immediate analysis of extracted soil cores and avoiding any requirements to transport the soil cores (which can induce structural and compositional (biochemical) changes in the soil) and thus reducing any changes in structure and/or loss of water content or other constituents from the soil cores. In some embodiments, the soil core multisensor platform component 102 includes a 3G or 4G mobile telecommunications network interface so that the operation of the system 100 can be controlled remotely, and the data acquired and/or generated by the soil core multisensor platform component 102 can be transmitted to cloud storage and/or the soil data analysis component 104 for real time analysis.

As shown in the flow diagram of FIG. 2, the system 100 is used to assess soil properties that determine soil organic carbon stocks and soil condition as a function of depth by analysing the sensor or measurement data recorded from the soil cores that are extracted from the ground at selected sampling locations of a region of interest (e.g., a farm property), using a drilling rig to extract the soil cores at step 202. In the described embodiments, intact soil cores with a diameter between about 45 to 85 mm are extracted. The extraction can be performed using, for example, a core extractor in the form of a push-tube (e.g., of a Geoprobe™ 7822DT drilling rig and DT325 sampling system with sample liners from Geoprobe, Salina, Kans., geoprobe.com). Each soil core can be sampled directly into a plastic liner within the push-tube. A longitudinal section of the liner is removed using a cutting tool (e.g. a Geoprobe™ DT325 liner cutter) to expose the soil core surface prior to analysis. If the soil cores are to be transported to a remote location for analysis, then the plastic core liner is left in-tact and sealed using end caps the plastic core liner is left intact and sealed using end caps. Alternatively, when using other coring systems, the soil core is removed from the push tube and slid into an elongate tube of thin plastic to prevent the soil core from drying out prior to analysis. Alternatively, each soil core can be extracted into a corresponding length of PVC pipe that has been halved longitudinally, and then the soil core and pipe wrapped in plastic to prevent moisture loss during transport. However, the portability of the soil core multisensor platform component 102 allows it to be transported to the region of interest so that each soil core extracted from that region can be immediately placed in the soil core multisensor platform component 102 and analysed without delay, if desired.

At step 204, an extracted soil core is received by the soil core multisensor platform component 102 by carefully placing it on the support bed or platform 304 in a horizontal orientation. At step 204, an operator of the soil core multisensor platform component 102 then enters desired core measurement parameters into the soil core multisensor platform component 102 by way of the touchscreen device (or keypad/keyboard input device, as the case may be) 112.

Figure 13:
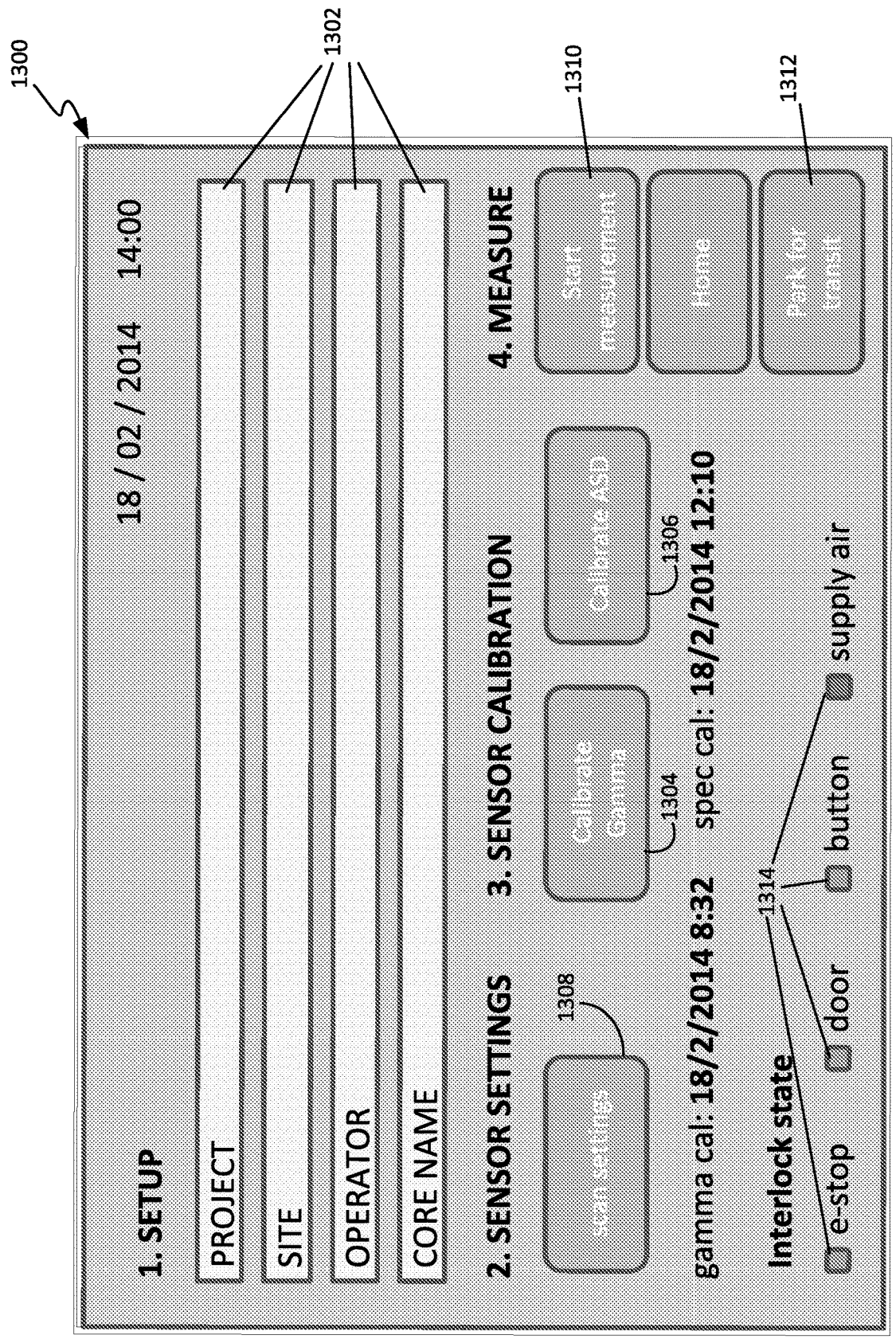
FIG. 13 is a screenshot of a graphical user interface (GUI) screen of the system, as displayed to an operator of the system when setting up a new measurement.

FIG. 13 is a screenshot of the initial graphical user Interface (GUI) or start screen 1300 displayed on the touchscreen device 112 when the system 100 is ready to commence a new measurement. The start screen 1300 includes text boxes 1302 that allow an operator of the system 100 to enter text data defining a name of the project of which this particular soil multisensor measurement is a part, the name of the site from which the soil core was extracted, the name or identifier of the operator, and the name or identifier of the particular soil core that is about to be measured. The "Calibrate Gamma" button control 1304 allows the operator to automatically calibrate the gamma ray attenuation sensor (typically, the radiometer is only calibrated once per day, prior to performing the first soil core measurement of that day). In embodiments where additional sensors/detectors/spectrometers/analysis components are included, the start screen 1300 includes additional button controls for calibrating the corresponding components, where calibration is required. The start screen visibly displays the status of the soil core mutisensor measurement system such as the state of the safety interlocks, supply air pressure and up-to-date sensor calibration. These conditions must be satisfied before the system allows a core measurement to be commenced.

Figure 14:
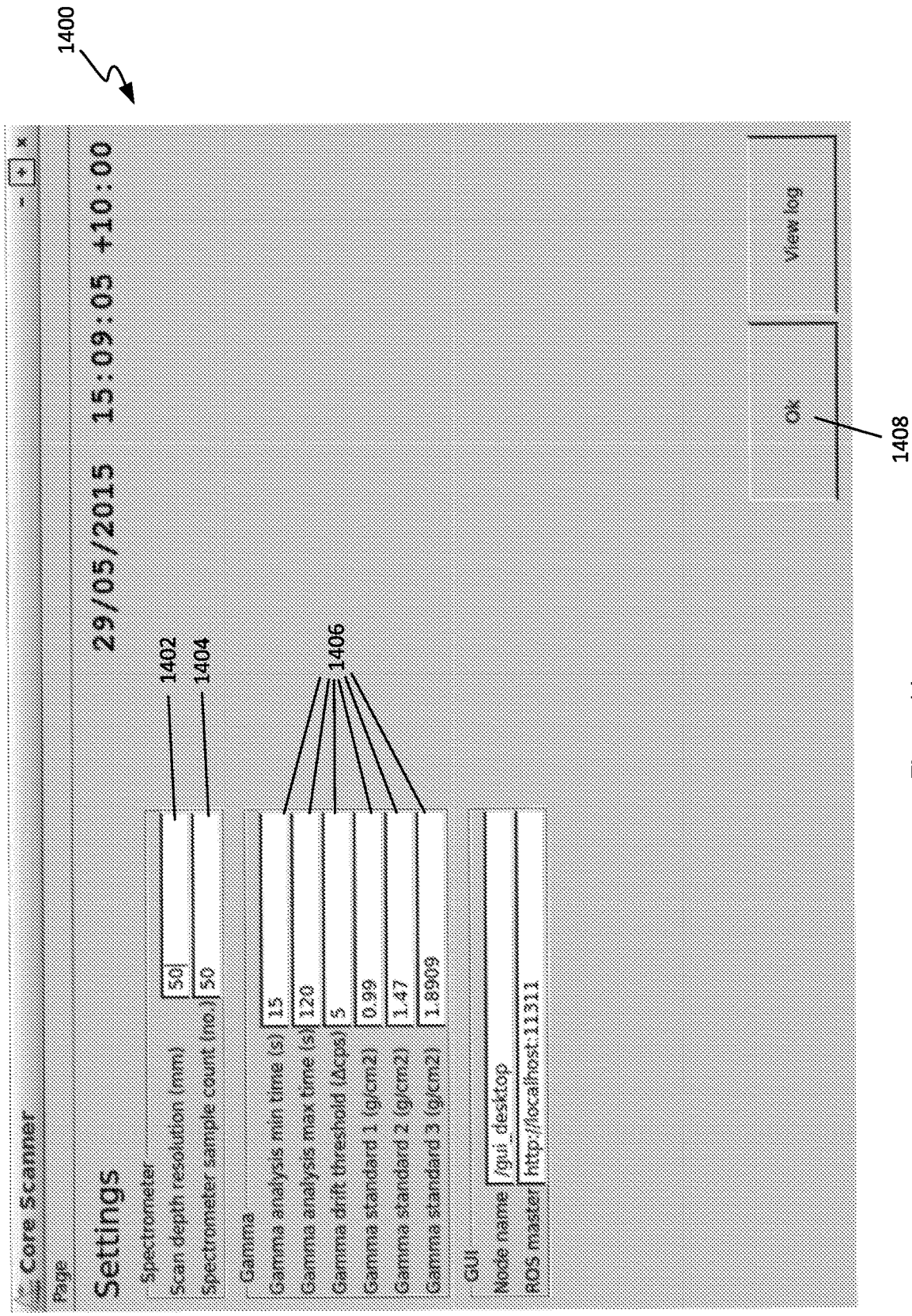
FIG. 14 is a screenshot of a "measurement settings" screen of the system.

A "sensor measurement settings" button control 1308, when touched (or pressed or clicked, as the case may be in other embodiments where an input device other than a touchscreen is used to provide input) by the operator, causes the touchscreen device 11 to 2 display a "sensor measurement settings" GUI or screen 1400, as shown in FIG. 14, which allows the operator to leave default values or define technical parameters of the core measurements, including the depth resolution (i.e., translation stage step size) and analysis parameters for each of the soil analysis components 308.

Alternatively, the operator can override the uniform step size using a 'sampling plan' text file that provides a list of values with the desired absolute measurement position on the core specified individually for each sensor. This can be used to optimise the soil core sensor measurement process for detail (resolution) and measurement time. For example, the analysis locations might be at equidistant positions along the soil core, or alternatively may vary with position/depth (e.g., measure every 1 cm from the surface to 30 cm, then every 5 cm from 30 to 60 cm, then 10 cm from 60 to 100 cm), between analysis locations along the length of the soil core, a typical value being 2 cm. Positions can be specified individually for each sensor to suit the characteristics of the sensor (e.g. capture digital images at 5 cm intervals only).

In the described embodiments, where the soil analysis components 308 include an optical spectrometer, the sensor measurement settings screen 1400 includes optical spectrometer text boxes 1404 into which the operator respectively enters the number of spectra (default value 50) to average for sensor calibration purposes and the number of measurement spectra (default value 30) to be acquired and averaged from the optical spectrometer during the spectroscopic measurements (to improve the signal-to-noise ratio). The spectrometer is automatically calibrated at the start of each core using a SPECTRALON® white reference standard that is fixed at a location on the core support rail. The optical spectra are recorded at a wavelength resolution of 1 nm and each spectrum provides values of reflectance at 2151 different wavelengths.

In the described embodiments, where the soil analysis components 308 include a gamma ray attenuation sensor, the sensor measurement settings screen 1400 also includes corresponding gamma ray analysis text boxes 1406 into which the operator can enter values to define the completion of a gamma attenuation measurement. Completion of a measurement can be specified in terms of signal drift (a drift threshold), although this criterion can be overridden for any measurement by specifying a minimum and maximum analysis time. The signal drift at a given time is assessed by performing a linear regression over the last five gamma density measurements. Once the resulting slope is less than the configured value of the drift threshold, then the gamma ray attenuation sensor is deemed to be sufficiently stable, and the gamma ray measurement therefore complete. The sensor measurement settings screen also includes text boxes in which the operator can enter the respective mass densities of the gamma attenuation calibration standards. Once the operator is satisfied with the soil core multisensor platform measurement parameters, the operator selects an "OK" button control 1408 to return to the start screen 1300.

Where the soil analysis components 308 include a gamma ray attenuation sensor, the start screen 1300 contains a 'calibrate gamma' control button which allows the operator to perform a calibration of the gamma-ray attenuation sensor. The operator is prompted to install calibration standards on the soil core support platform 304. The operator can initiate the calibration by selecting the 'start' button. The linear translation stage 310 is moved by the control computer 110 to determine the absolute position of the calibration standards on the support platform 304 using optical proximity sensors (not shown) installed on the linear translation stage 304.

From the start screen 1300 the user can then select a "start measurement" button controls 1310 in order to initiate automatic soil core measurements and data acquisition of the soil core at step 208, under control of the control computer 110.

In the described embodiments, the sensor measurement control sub-system 108 is an Advantys™ STB modular device integration I/O system manufactured by Schneider Electric, as described at http://www.schneider-electric.com. The Advantys™ system allows up to 32 modules of various types to be interconnected with a common communications bus, providing power and digital and analog signal distribution to and from the various sensing and analysis hardware components 106, using USB and RS-232 communications protocols and connections (Ethernet is also available, where required). The Advantys™ system thus provides an interface between the sensing and analysis hardware components 106 and the control computer 110. The Advantys™ system configuration of the system 100 is shown in FIG. 4.

The Advantys STB interfaces with the control computer (via Ethernet to the advantis node 506) and with following system components:
Inputs:
Core detect sensor (optical proximity sensor)
Air pressure gauge
e-stop button state
e-stop status (from PNOZ)
Optical spectrometer sensor position—the control software checks this (i.e., that the sensor is in the up position) before moving the linear stage to prevent damage to the core or the optics
Outputs:
Front panel indicator lamp (enabled) with the e-stop and reset button
Pneumatic control of the gamma-ray source shutter
Core detect (optical proximity sensor) enable
Pneumatic control of the optical spectrometer sensor
LED illumination for the digital camera Data acquisition from the soil analysis components 308 is handled directly by the control computer, interfaced as follows: Optical spectrometer (via ethernet), Gamma-ray attenuation sensor (via RS232), and Digital camera (via USB). The accelnet node 502 of the control computer 110 communicates with the Accelnet motor driver using the RS232 interface 1614. All multisensor platform control (apart from the independent safety interlocks) is handled by the scanner_controller node 512 of the control computer 110.

Figure 12:
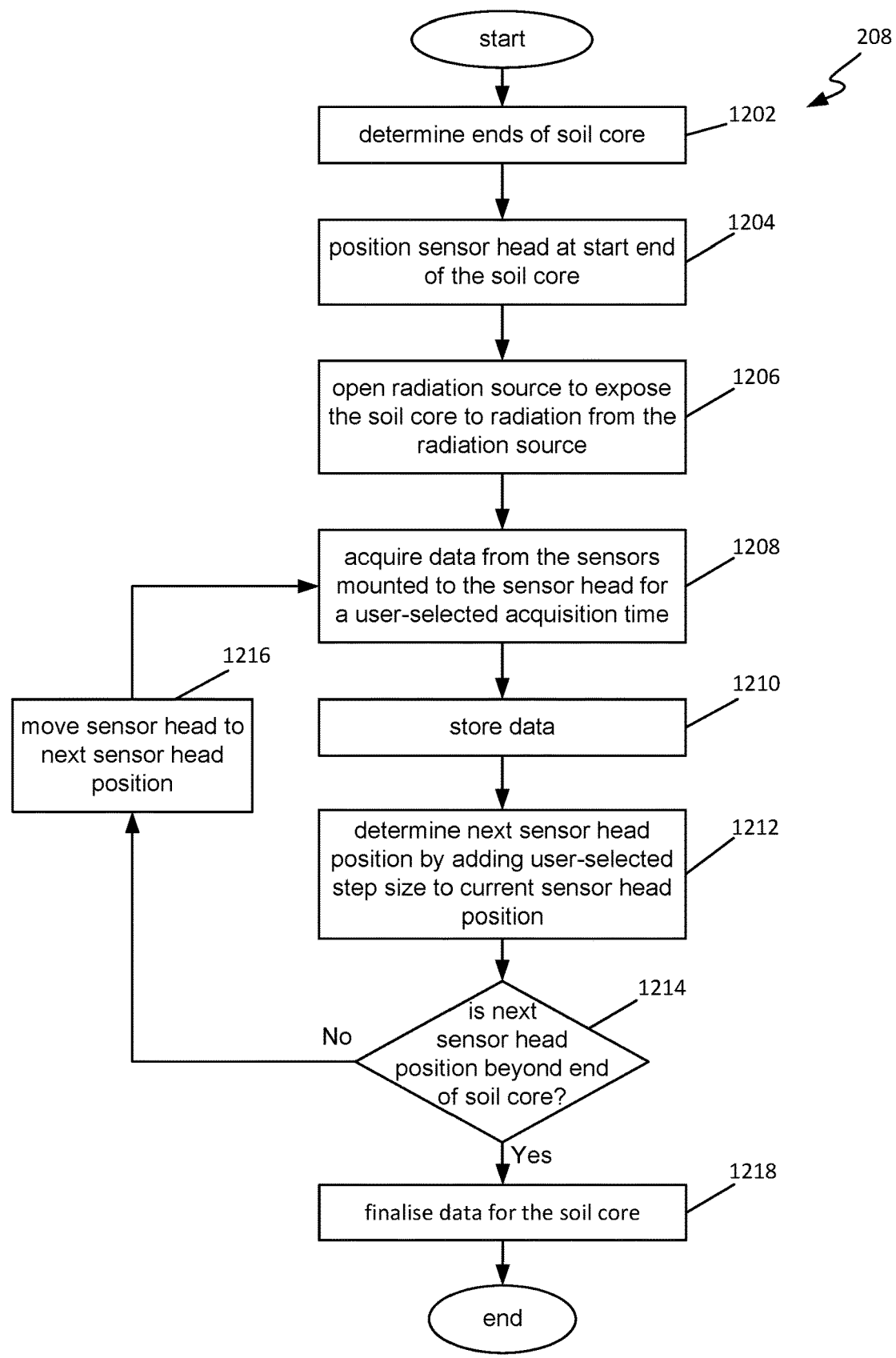
FIG. 12 is a flow diagram of a soil core multisensor platform measurement process of the process of FIG. 2.

The core multisensor platform measurement process 208, as shown in FIG. 12, is implemented by the scanner_controller node 512 and is executed by at least one processor of the control computer 110. Where the soil analysis components 308 include an optical spectrometer, the core multisensor measurement process 208 begins by automatically calibrating the optical spectrometer. The linear translation stage 310 is moved by the control computer 110 to a fixed position where a suitable optical reference panel (SPECTRALON® white reference panel) is installed on the core support rail 304. A reference measurement is collected using the optical spectrometer and used to correct subsequent measurements of the current soil core.

The core multisensor platform measurement process 208 continues (or begins in embodiments that do not contain an optical spectrometer) at step 502 by automatically determining the locations of the two ends of the soil core and from these the length and position of the soil core. The linear translation stage 310 is moved by the control computer 110 along the core support platform and the soil core is detected using an optical proximity sensor installed on the linear translation stage. Position is determined with the use of an optical encoder positioned on the motor.

Having identified the absolute positions of the two ends of the soil core with respect to the support bed platform the control computer 110 calculates a 'sampling plan' consisting of the absolute measurement positions and corresponding sensor measurements to collect measurements on the soil core at the positions and resolution specified by the operator in the sampling plan. The control computer uses pre-programmed offset measurements from a datum on the linear translation stage to account for sensors that are not co-located. The offset of each sensor is recorded relative to the sensor head datum, which is defined as the position of the main mounting plate. These configuration parameters are all stored on the core multisensor platform PC. Once the core detect process completes, the sensor offsets and the measurement plans are used to calculate each absolute measurement position. If absolute head positions align for multiple sensors, then these measurement acquisitions are performed concurrently. The next measurement position is chosen as the next closest absolute location on the core to reduce head travelling time.

Figure 15:
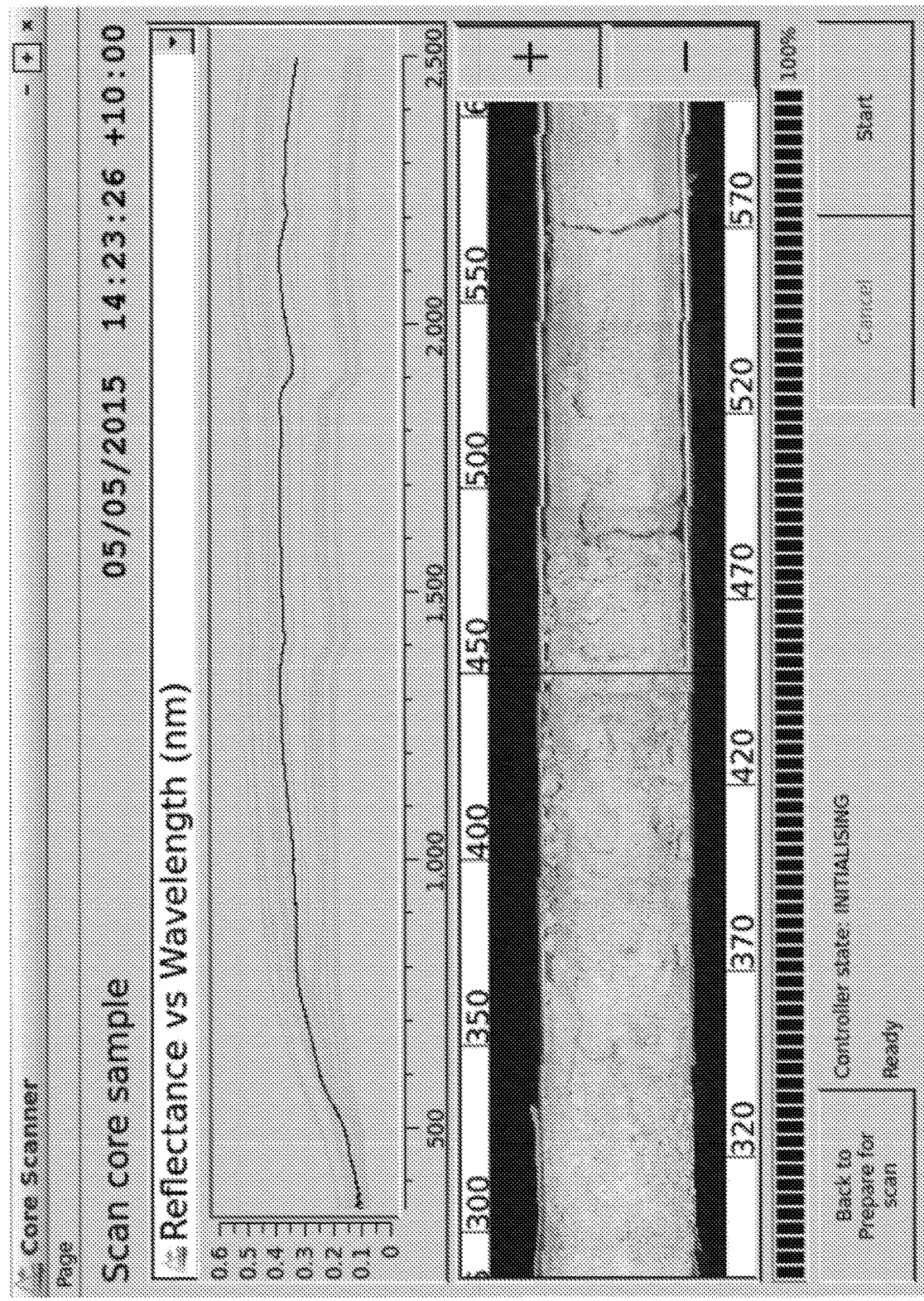
FIG. 15 is a screenshot of a "measurement" screen of the system displayed to the operator during the measurement of a soil core, showing a photographic image of the soil core with an indicator showing the current depth/location along the core being analysed, above which is displayed an analysis spectrum for that depth/location.

At step 504, the sensor head is moved to a fixed 'start' position on the core support platform. The control computer 110 then determines the closest sampling location in the 'sampling plan' from its current position. The linear translation stage 310 is moved by the control computer 110 to this position and measurement using the required sensors for this position is commenced. Where multiple sensor measurements can be performed at the same sensor head position (accounting for any relative offsets between the sensors), these are collected in parallel to reduce the overall measurement time. At step 506 where the soil analysis components 308 include a gamma-ray attenuation sensor and a gamma-ray attenuation measurement is to be performed at this measurement location, the protective shutter on the radiation source is opened. This shutter remains open until all gamma-ray attenuation measurements have been completed. If the control computer 110 determines that the gamma-ray attenuation sensor has exceeded the end positions of the soil core, then the protective shutter is closed to prevent damage to the detector. A digital image of the corresponding portion of the soil core is displayed on the touchscreen display 112 of the multisensor platform control component, together with the spectrum that is currently being acquired from a user-selected one of the soil analysis components 308, overlaid onto any spectra that have been previously acquired from the same soil analysis component during the multisensor measurements, these spectra being displayed in grey whereas the spectrum being acquired is displayed in black, as shown in FIG. 15. In addition, the operator can use the touchscreen (or other input means) to select any other depth/position along the soil core in order to display the corresponding spectra previously acquired at the selected depth/position. Additionally, the operator can select from a pull-down menu any one of the soil analysis components 308 in order to display the corresponding measurement (e.g. spectra, density, counts) from the selected soil analysis component.

Figure 25:
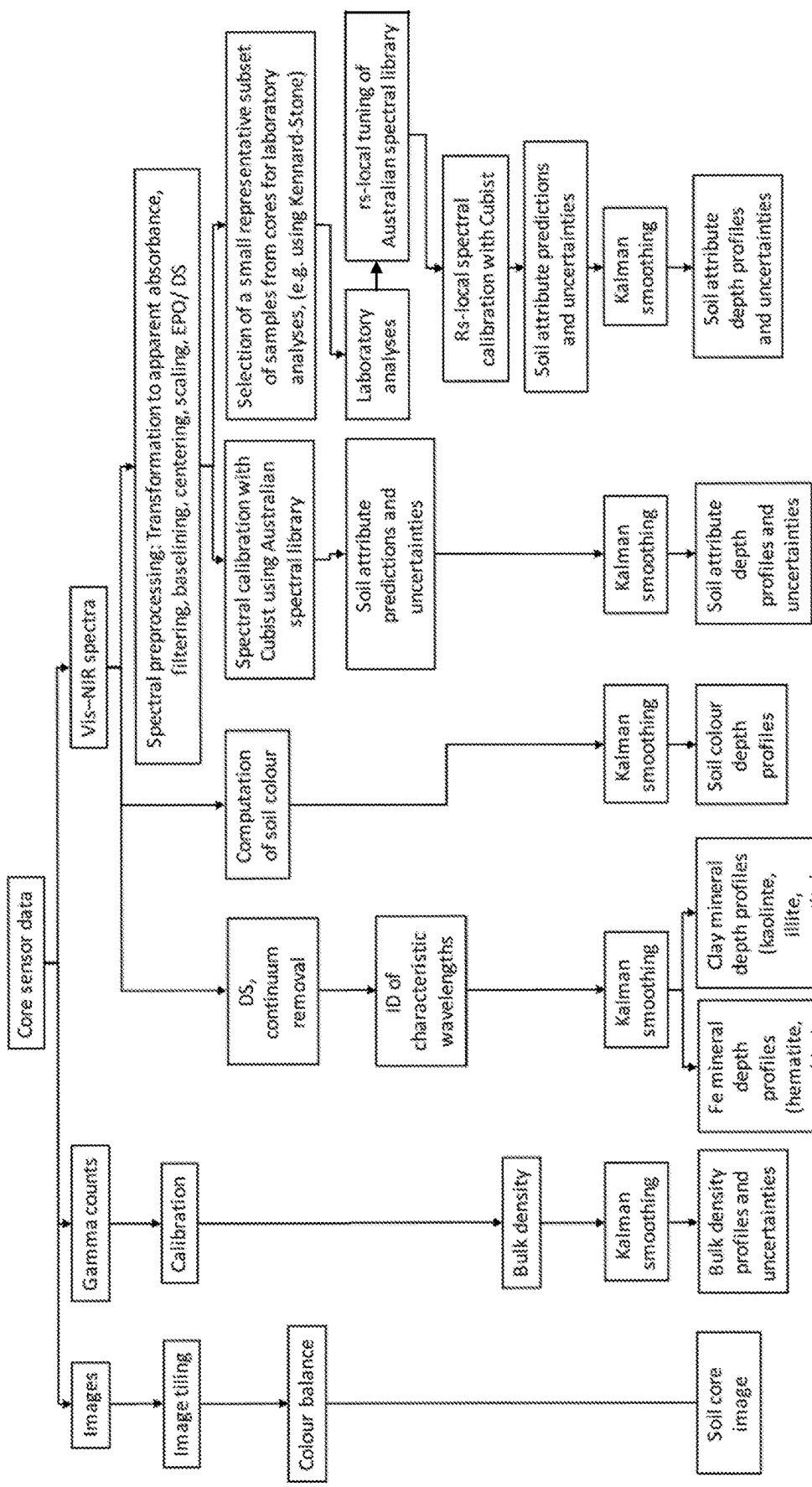
FIG. 25 is a flow diagram of a soil core data analysis process of the system.

All the sensor measurements are stored in the control computer 110 RAM during the multisensor platform measurement process. At step 512, the next position of the sensor head is determined as the closest unsampled position in the 'sampling plan'. The linear translation stage 310 is moved by the control computer 110 to this position and measurement data is collected from the appropriate sensors at this location. If there is no remaining sample locations in the 'sampling plan' the process 208 then completes. On the completion of sensor measurements for a soil core, the acquired data for the entire soil core (together with metadata providing the core identity, vis-NIR and gamma-ray sensor calibrations, project, site and operator names, date and time) is stored in a hierarchical directory/folder structure (based on the project name) on the control computer 110. Referring to the flow diagram of FIG. 2, the process 200 proceeds to process all of the acquired data for the soil core using a soil core data analysis process 210, as shown in FIG. 25.

The multisensor platform measurement process can be terminated by the operator in software using the 'cancel' button or in hardware by activating the emergency stop (using the e-stop button) or by opening the protective hood of the multisensor platform. If the multisensor measurements are terminated using the cancel button or e-stop button the multisensor measurements can resume from its previous state using the 'start' button. If the protective hood of the soil core multisensor platform is opened at any point the absolute position of the core on the support platform is invalidated as it may have been moved by the operator. The multisensor measurement process will then recommence at step 502.

As shown in FIG. 6, soil core data analysis process 210 begins at step 602 by stitching together the images acquired by the digital camera to generate a single colour digital image of the entire soil core. Individual images are stored separately for later processing. However, during the multisensor measurements the visualisation system performs a simple real-time tiling of images. Because the sampling locations are known, and the height above the core is constant, the tiling overlap is approximated as a function of sample position. The exact function is configured visually via feedback in the graphical user interface to handle any variations in camera position and field of view. Each individual image is corrected for rotation, a subimage is extracted, and all subimages are stitched together to produce a composite full image of the soil core. The camera sampling plan remains fixed (i.e., it does not follow the user-supplied sampling plan because it is mainly used to get the image of the core for visualization purposes only). The overlap only requires reconfiguring if the camera position is changed, or if a new camera is used.

At step 604, the core image are further analysed to provide additional information using computer vision techniques to extract visible RGB colour measurements and relating them to other colour space models and soil properties (as described in Viscarra Rossel, R A, Minasny B, Roudier, P, McBratney, A B. 2006, *Colour space models for soil science*, Geoderma 133: 320-337).

The data from the gamma and optical sensors are used to infer soil properties along the soil core at the measurement locations (which are determined by the user), as follows.

Vis-NIR Measurements

The vis-NIR spectrometer measures the organic and mineral compositions of the soil core. When NIR radiation interacts with a soil sample, the overtones and combinations of fundamental vibrations in the mid-infrared (mid-IR) region are detected. Molecular functional groups can absorb in the mid-IR, with a range of progressively weaker orders of overtones detected in both the mid-IR and NIR regions. In the visible region, electronic excitations are the main processes as the energy of the radiation is high. vis-NIR spectra contain useful information on organic and inorganic materials in the soil. Absorptions in the visible region (400-700 nm) are primarily associated with organic matter and minerals that contain iron (e.g., haematite, goethite). Soil organic matter can also have broad absorption bands in the visible region that are dominated by chromophores and the darkness of organic matter. Absorptions in the NIR region (700-2500 nm) result from the overtones of OH, $SO_4$, and $CO_3$ groups, as well as combinations of fundamental features of $H_2O$ and $CO_2$. Clay minerals can show absorption in the vis-NIR region due to metal-OH bend plus O—H stretch combinations. Carbonates also have weak absorption peaks in the near infrared. Water has a strong influence on vis-NIR spectra of soils. These data can therefore be modelled to infer soil properties.

To estimate soil properties using the vis-NIR spectra, general spectroscopic models are derived using the Australian spectral library (described in Viscarra Rossel, R. A., Webster, R., 2012, *Predicting soil properties from the Australian soil visible-near infrared spectroscopic database*, European Journal of Soil Science 63, 848-860. doi:10.1111/j.1365-2389.2012.01495.x). The spectroscopic models are developed using the machine learning algorithm Cubist (as described in Quinlan, J., 1992. Learning with continuous classes., in: Adams, A., Sterling, L. (Eds.), Proceedings AI'92, 5th Australian Conference on Artificial Intelligence, World Scientific, Singapore. pp. 343-348). These models allow the simultaneous estimation of volumetric water content ($\theta$), organic C, clay content, cation exchange capacity (CEC), pH, total nitrogen, total phosphorus, iron content, water content, and a number of other soil properties. The Australian soil organic carbon fractions (particulate, humic and resistant C) are estimated using the Australian carbon vis-NIR fractions library (described in Viscarra Rossel, R. A., Hicks, W. S., 2015, *Soil organic carbon and its fractions estimated by visible-near infrared transfer functions*, European Journal of Soil Science 66, 438-450. doi:10.1111/ejss.12237)). Available water capacity can be estimated using a soil water library developed for Australian soils.

The estimates of the soil properties are derived using different approaches for the spectroscopic modelling, which depend on the availability of local data and the application. In the absence of any local data (i.e. data from the same geographic location, e.g. a field), estimates of the soil properties are made with Cubist models derived using the Australian soil property spectral library, the soil organic C fractions library, and the soil water library described above.

Conversely, when local samples are available, calibrations are developed using the 'rs-local' method described below, which uses a small number of representative local samples with a well-selected subset of the large spectral library for the calibrations with CUBIST. A more extensive discussion of the rs-local method and comparison with other methods and validation of the method are provided in Lobsey, C., Viscarra Rossel, R., Roudier, P., and Hedley, C. 2016, *Can Large soil spectra libraries improve local calibrations of soil organic carbon?*, submitted to the European Journal of Soil Science ("Lobsey I")), the entirety of which is hereby incorporated herein by reference.

The 'RS-Local' Method

The 'rs-local' method uses re-sampling to evaluate and then remove individual spectra from a soil spectral library (e.g. the Australian spectral libraries described above) so that the spectra that remain are the most appropriate for deriving a local calibration. The method requires only a small local data set that is representative of the site, selected with, for example, the Kennard-Stone, or DUPLEX algorithms (Kennard and Stone, 1969; Snee, R. D., 1977. Validation of regression models: methods and examples. Technometrics, 19(4), 415-428).

The rs-local method proceeds as follows for each 'target' soil parameter of interest:

(i) initialise K as a subset of the soil spectral library, with K initially containing the entire library;
(ii) A training data set of size k, is sampled from K by random sampling (without replacement on the first execution immediately after step (i) only, and with replacement on each subsequent repeat (looping from step (v));
(iii) Using the training data set k, a partial least squares regression (PLSR) is derived to predict the target soil property;
(iv) The model is validated using the local data set, and the root mean square error (RMSE) of this validation is generated and assigned to the selected k samples;
(v) steps (ii) to (iv) are repeated B times. Whereas k was previously sampled without replacement in step (ii), these samples are replaced before each repeat. The root mean square error (RMSE) generated at step (iv) is cumulatively assigned to each selected sample over the B repeats.

B=length(K)$\times$(b/k), where b is the number of times a sample should be drawn (tested) after B repeats;
(vi) The spectral library subset K is ranked by the cumulative RMSE, and a proportion of samples r with the largest cumulative RMSE values (i.e. those samples that are consistently used in the poorest performing models) are removed from the SSL subset. r is defined as a fixed proportion of the spectral library subset so that the amount removed becomes progressively smaller as the size of the spectral library decreases. The number of times each sample is selected over the B repeats is tracked and used to normalise the cumulative RMSE before removing the samples;
(vii) The remaining samples in the spectral library subset are retained, and form part of a new, more specific, customised or 'tuned' spectral library subset K;
(viii) Steps (i) to (vii) are repeated until the spectral library has reduced in size such that k can no longer be sampled i.e. until the size of K equals k$\times$(1+r);
(ix) Once the 'tuned' spectral library subset has been derived, the local data set in step (iv) is used to augment it by spiking, and the local calibrations are determined to predict the target attribute.

A pseudo-code implementation of the method is as follows:

```
1: procedure RS-LOCAL(m, SSL, b, k, r)
2:      K ← SSL                        ▷ Initialise SSL subset to full SSL
3:      while size(K) > (k * (1 + r)) do
4:          L ← size(K)
5:          U⁰ ← 0^L                   ▷ Vector to track cumulative RMSE
6:          V⁰ ← 0^L                   ▷ Vector to count sample tests
7:          B ← L * (b/k)              ▷ Calculate number of B iterations
8:          for i = 1 : B do
9:              K_sample ← sample(K, size = k)
10:             mod ← calibrate(SSL_sample)
11:             rmse ← validate(mod, m)
12:             U^Ksample ← U^Ksample + rmse
13:             V^Ksample ← V^Ksample + 1
14:         end for
15:         U ← U/V                    ▷ Normalise cumulative RMSE by tests
16:         K ← K * (1 − r)            ▷ remove r highest values
17:     end while
18:     return K                        ▷ Return the selected SSL subset
19: end procedure
```

To implement rs-local, three parameters need to be determined. They are k, the number of training samples to draw from the spectral library subset for modelling, b the number of times a sample will be drawn over the B repeats, and the ratio r of the spectral library subset that is removed every time a new spectral library subset is drawn form the spectral library. As described in Lobsey I, recommended parameter values for r and b are r$\leq$0.2; b$\geq$20. Smaller values for r and larger values for b increase computation time. Values for k were consistent across the range tested by Lobsey et al. but they used k=300.

Soil colour is also measured using different colour space models as described above, and the relative abundances of hematite, goethite, kaolinite, illite and smectite are estimated from the widths and heights of their corresponding specific absorptions on continuum-removed spectra, as described in Viscarra Rossel R. A., Cattle S. A, Ortega A, Fouad, Y. In situ measurements of soil colour, mineral composition and clay content by vis-NIR spectroscopy Geoderma 150 (2009) 253-266 doi: 10.1016/j.geoderma.2009.01.025; and Clark, R. N., Roush, T. L., 1984. Reflectance spectroscopy: Quantitative analysis techniques for remote sensing applications. Journal of Geophysical Research: Solid Earth 89, 6329-6340. doi:10.1029/JB089iB07p06329).

When used in the field, soil vis-NIR spectroscopy can be affected by water at absorption wavelengths near 1400 and 1900 nm. To enable in-field analysis with soil cores under field condition, the system uses either external parameter orthogonalisation (EPO) (as described in Roger, J. M., Chauchard, F., Bellon-Maurel, V., 2003, *Epo-pls external parameter orthogonalisation of PLS application to temperature-independent measurement of sugar content of intact fruits*, Chemometrics and Intelligent Laboratory Systems 66, 191-204. doi:10.1016/50169-7439(03)00051-0; and in Minasny, B., McBratney, A. B., Bellon-Maurel, V., Roger, J. M., Gobrecht, A., Ferrand, L., Joalland, S., 2011, *Removing the effect of soil moisture from nir diffuse reflectance spectra for the prediction of soil organic carbon*, Geoderma 167-168, 118-124. doi:10.1016/j.geoderma.2011.09.008) to project spectra orthogonal to variations induced by water, or direct standardisation (DS) to transfer the wet field spectra so that it may be predicted with the laboratory-derived spectral library (as described in Ji, W., Viscarra Rossel, R. A., Shi, Z., 2015, *Accounting for the effects of water and the environment on proximally sensed vis-NIR soil spectra and their calibrations*, European Journal of Soil Science 66, 555-565. doi:10.1111/ejss.12239).

Uncertainty in the spectroscopic modelling is estimated using bootstrap re-sampling (as described in Viscarra Rossel, R., 2007, *Robust modelling of soil diffuse reflectance spectra by bagging-partial least squares regression*, Journal of Near Infrared Spectroscopy 15, 39-47. doi:10.1255/jnirs.694). This technique uses random sampling with replacement to generate multiple training data sets for the spectroscopic modelling. These models are used to estimate different realisations of the soil property to form cumulative distribution functions for each estimate, from which mean and confidence intervals are determined.

Soil Densitometry

The gamma ray attenuation sensor includes a radioactive ($^{137}$Cs) source to emit γ-rays into the cylindrical soil core along a radial direction, and a γ-ray detector to detect those γ-rays that pass through the cylindrical soil core without being absorbed by the core or scattered out of the acceptance angle of the detector. The ratio of the detected number of gamma rays passing through the soil core to the detected number when the soil core is not present between the source and detector is referred to as gamma-ray attenuation, and provides a direct measure of the soil's apparent density at the corresponding location along the core.

The attenuation of gamma-ray radiation passing through a soil core is given by Beer Lambert's law, as follows:

$$\frac{I}{I_0} = \exp(-x(\mu_s, \rho_{b_s})),$$

where I is the attenuated radiation at the detector after passing through the soil core, $I_0$ is the unattenuated radiation (i.e., when no soil core is present), and x is the sample thickness. The parameters $\mu_s$ and $\rho_{b_s}$ represent the mass attenuation in cm$^2$ g$^{-1}$ and the density of the soil in g cm$^{-3}$, respectively. The mass attenuation of soil, $\mu_s$, is a function of its elemental constituents, and therefore the attenuation is affected by the sample's texture and mineralogy. However at high energies (e.g. 0.662 MeV) these effects are insignificant.

To measure the bulk density of soil under field conditions, it is necessary to account for the mass attenuation of soil water at the corresponding gamma ray energy, in the case of a $^{137}$Cs source, being 0.662 MeV. For a heterogeneous sample (i.e., a wet soil core), the measured attenuation is given by:

$$\frac{I}{I_0} = \exp[-x(\mu_s\rho_s + \mu_w\rho_w\theta)]$$

where I and $I_0$ are the incident and attenuated radiation, respectively, x is the effective path length or core thickness in cm. The parameters $\mu_s$ and $\mu_w$ are in units of cm$^2$ g$^{-1}$ and represent the mass attenuation coefficients of the soil and water respectively. The parameter $\rho_w$ is the density of water, which is 1 g cm$^{-3}$ and θ is the volumetric water content of the soil in cm$^{-3}$ cm$^3$. The effective path length or core thickness accounts for the curvature of the soil core, and is determined using cylindrical calibration standards having the same diameter as the soil core. The mass attenuation coefficient of soil $\mu_s$ depends on both the photon energy and its elemental constituents. However, at high photon energies (e.g., 0.662 MeV), the effects of varying soil composition become negligible (as described in Luo, X., Wells, L., 1992, *Evaluation of gamma-ray attenuation for measuring soil bulk density*, I. Laboratory investigation. Transactions of the ASAE 35). The system use values of the soil and water mass attenuation coefficients derived in Lobsey, C., Viscarra Rossel, R., 2016. Sensing soil bulk density for more accurate carbon accounting. European Journal of Soil Science ("Lobsey II"), the entirety of which is hereby incorporated herein by reference.

Therefore, the dry bulk density of the soil, $\rho_{bs}$, can be determined once values for the parameters $I_0$, $\mu_s$ and $\mu_w$ are known, and an independent measure of θ. The vis-NIR spectra are used to infer θ using the spectroscopic modeling described below. The bulk density of the soil cores when wet is determined by solving for $\rho_{bs}$ $$\rho_{b\gamma} = \frac{1}{x\mu_s}\ln\left(\frac{I_0}{I}\right) - \frac{\mu_w}{\mu_s}\rho_w\theta,$$

where θ is inferred from the vis-NIR spectra.

X-Ray Fluorescence (XRF) and X-Ray Transmission (Attenuation) Measurements

As described above, in some embodiments the soil analysis components 308 include an x-ray fluorescence (XRF) analysis component to measure the elemental composition of the soil core at each sampling depth/location along the core. XRF relies on the fluorescence at specific energies of atoms that are excited when irradiated with X-rays. In some embodiments the soil analysis components 308 include an x-ray sensor for transmission measurements through the soil core. In some embodiments, the XRF analysis component is an AMPTEK X-123SDD Complete X-Ray Spectrometer with Silicon Drift Detector (SDD). It uses the Mini-X self-contained miniature X-ray tube, which is designed to replace radioisotopes in X-ray fluorescence analysis applications. Detection of the specific fluorescent photons enables the analysis of the elements in a sample. In air, the instrument can detect elements with atomic weights larger than 25 (i.e. it can just detect aluminium). In a vacuum, the XRF analysis component can measure lighter elements.

The result of the process 200 is a set of data representing estimates of the soil properties such as organic carbon content, carbon composition (particulate, humic and resistant organic carbon), bulk density, carbon stocks, soil water, available water capacity, clay content, total nitrogen, iron and clay mineralogies, soil colour, cation exchange capacity, pH, which aid to define the condition of the soil as a function of depth for the geographical location at which the soil core was removed.

In general, embodiments of the soil measurement systems and processes described herein can measure key soil properties that define the condition of soil, including: bulk density (measured with the gamma sensors and with water corrections from the spectroscopic measurements of water, as described above) and soil organic carbon, carbon composition (particulate, humic and resistant organic carbon), clay content, total nitrogen, water content, available water capacity, clay and iron oxide mineral abundances, soil colour, cation exchange capacity, pH, which help to describe soil and its condition.

By performing spectroscopic modelling with the bootstrap Monte-Carlo method, the spectroscopic measurements can be derived with estimates of uncertainty. These uncertainty estimates are used with a Kalman smoothing algorithm to derive improved or filtered estimates of the above soil properties with depth, while also providing corresponding measures of uncertainty in these estimates. The Kalman smoothing algorithm is described in Grewal M S and Andrews AP (1993), *Kalman Filtering Theory and Practice*, Prentice Hall Information and System Sciences Series, Prentice Hall. The Kalman filter has a key advantage over other techniques for deriving soil property profiles (e.g. spline interpolation), in that it allows the uncertainty in the sensor measurements to be incorporated in the process and thus enables its propagation to the filtered estimate.

The described embodiments use the implementation of Kalman smoothing provided in the KFAS package (as described in Helske, J., 2016. KFAS: Kalman Filter and Smoother for Exponential Family State Space Models. URL: http://cran.r-project.org/package=KFAS. r package version 1.2.1) in the R software (R Core Team, 2016. R: A language and environment for statistical computing. R Foundation for Statistical Computing. Vienna, Austria. URL: http://www.R-project.org).

For any soil property, x (e.g. soil organic C), along a soil core, sensor measurements begin at the soil surface, and are made at defined depth intervals k. These measurements are imprecise, but it is desired to maintain a model that defines the magnitude of x along the soil core and its rate of change with depth. Thus, the linear state space $x_k$ is defined as:

$$x_k = \begin{bmatrix} x \\ \dot{x} \end{bmatrix} \quad (3)$$

where $\dot{x}$ is the rate of change of soil property with depth. Note that k is assumed to be discrete (i.e. fixed measurement intervals), although this can vary depending on the measurement configuration defined by the user as described above. Then, the state transition model between the (k−1) and k depths, is defined by:

$$x_k = \begin{bmatrix} 1 & \Delta k \\ 0 & 1 \end{bmatrix} x_{k-1} + w_k, \quad (4)$$

where $w_k \sim N(0, Q_k)$, is the process noise, which is assumed to be normally distributed with variance $Q_k$. It can be fixed or derived using maximum likelihood estimation (MLE) (see Helske, J., 2016. KFAS: Kalman Filter and Smoother for Exponential Family State Space Models. URL: http://cran.r-project.org/package=KFAS. r package version 1.2.1).

At each depth, a noisy measurement, $z_k$, of the true soil property value is made with the particular sensor so that the observation model can be defined by:

$$z_k = [1 \ 0] x_k + v_k, \quad (5)$$

where $v_k \sim N(0, R_k)$ is the observation noise that is assumed to be normally distributed with variance $R_k$. For the spectroscopic estimates of soil properties, the respective spectroscopic model bootstrap variances are used. For the gamma-ray attenuation measurements $R_k$ is the sum of two components. The first represents a standard error for gamma-ray attenuation measurements of 0.029 g cm$^{-3}$ (as described in Lobsey II), and the second is the bootstrap variance of the spectroscopic estimate of volumetric water content used in the correction (see above and Lobsey II). The method then recursively predicts the soil property at the particular depth using only the previously estimated state and the sensor measurements at the current depth and its uncertainty matrix. A more extensive discussion of this method is provided in Viscarra Rossel, R. A., Lobsey, C, Sharman, C., Flick, P., McLachlan, G. 2016. The Soil Condition ANalysis System (SCANS) quantifies the attributes of soil profiles to deepen our understanding of soil (submitted to European Journal of Soil Science), incorporated herein in its entirety by reference.

The soil measurement systems and processes described herein can thus be used to effectively assess soil condition, stocks of soil carbon content and composition and aspects of soil fertility to depth, for e.g. precision agriculture and the assessment of contaminated sites.

In an alternative embodiment, the sensor head holds four sensors, including the vis-NIR spectrometer and active gamma-ray attenuation sensor described above, a camera module built from a Raspberry Pi 2 single board computer (Raspberry Pi Foundation, https://www.raspberrypi.org/), a 5 megapixel Raspberry Pi camera and a Lepton long wave infrared camera (FLIR Systems, Oregon, US).

In this embodiment, the visible and LWIR camera are interfaced to a second computer 1902, namely a small single-board computer that in turn is interfaced to the first or 'main' computer 1600 described above. In the described embodiment, the single-board computer is a Raspberry Pi 2 single board computer connected to the main computer 1600 via Ethernet, and the visible camera is a 5 megapixel Raspberry Pi camera. However, it will be apparent to those skilled in the art that other types of computer, interconnection methodologies and protocols, and peripheral types may be used in other embodiments. The soil core is illuminated by LED lighting installed on the camera.

Figure 18:
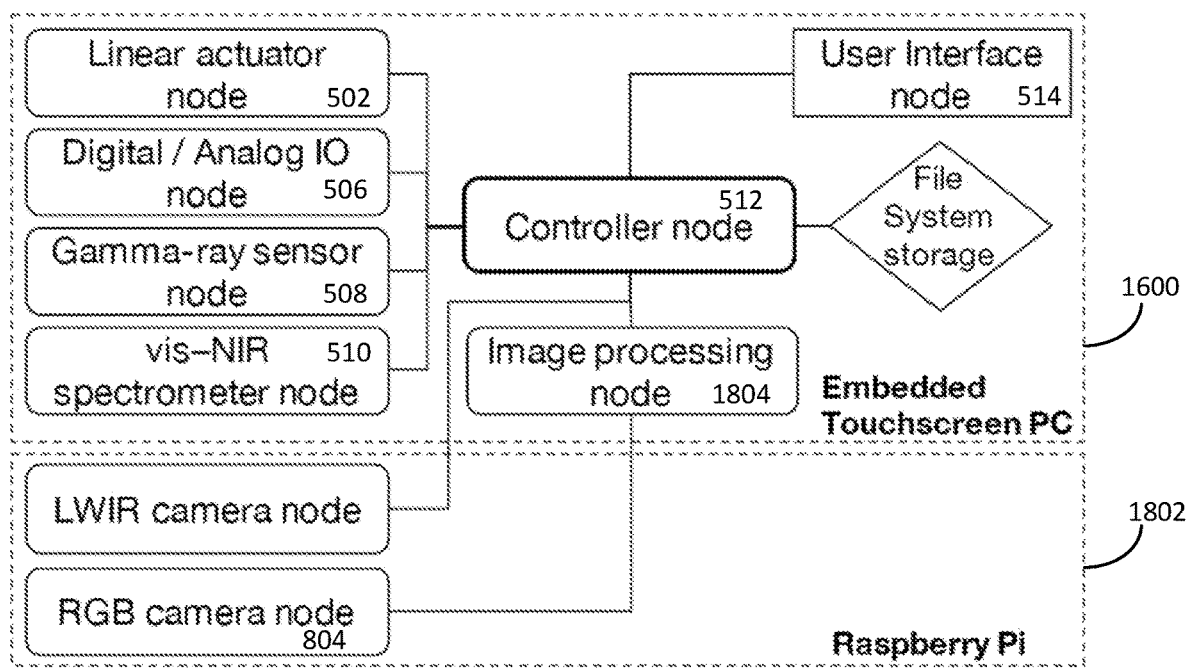
FIG. 18 is a block diagram showing ROS nodes of the system and their distribution between two computer systems in accordance with an alternative embodiment of the system.

As with the first embodiment described above, the processes executed by the system are implemented as ROS packages. However, in the second embodiment, the ROS nodes are distributed across the two computers 1600,1902, as shown in FIG. 18. The main computer 1600 hosts most of the sensor interfacing software, multisensor platform measurement logic, data storage and graphical user interface, and also the ROS master node (not shown) which provides a register for other nodes to discover each other. In the described embodiment, the second (Raspberry Pi) computer 1902 is used exclusively to interface with the RGB and LWIR cameras, and thus includes the RGB camera node 504, and a LWIR camera node 516, and communicates with the main computer 1600 via Ethernet. In the described embodiment, each computer 1600,1902 runs a Linux™ operating system.

Figure 19:
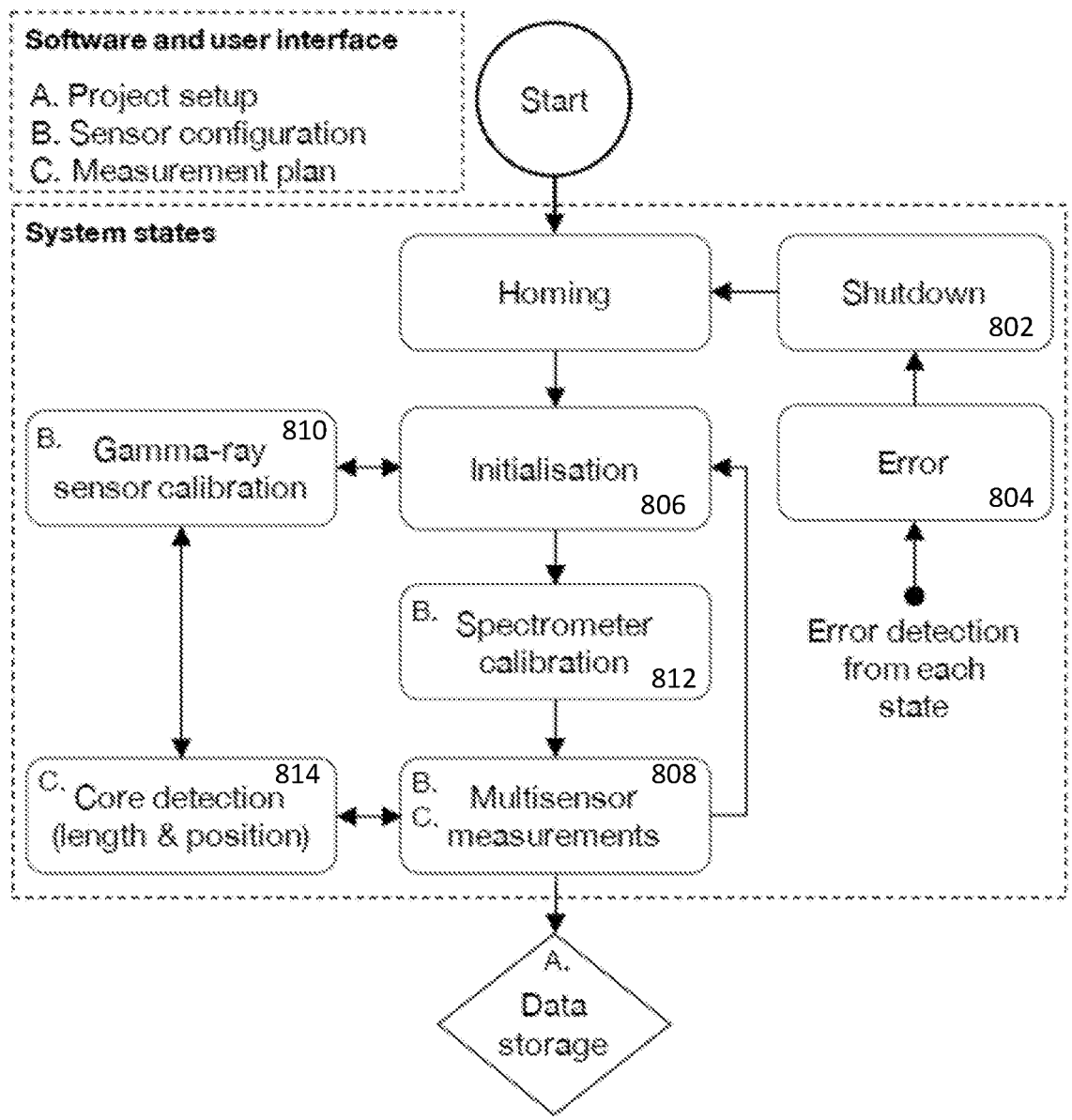
FIG. 19 is a state diagram showing the various operating states of the system of the alternative embodiment.

In this embodiment, the measurement process is implemented as a finite state machine with eight distinct states 902 to 816, as shown in FIG. 19. The state flow supports safe operation of the multi-sensor platform, if a safety condition is breached at anytime (e.g. the protective door is opened), the measurement controller will immediately move to its shutdown state 802 via an Error State 804. The state machine design also ensures quality control, with the controller node only progressing to an initialisation state 806 once it has confirmed that all sensor nodes are operating.

Progressing to the sensor measurements state 808 is only possible after the gamma-ray attenuation sensor has been calibrated in state 810, and the locations of the opposing ends of the elongate soil core have been determined at state 814. Calibration is configured with a maximum age which forces the operator to perform a calibration after a fixed period, defined by the time elapsed since the previous calibration. Before the first sensor measurements on each soil core, the controller enters the vis-NIR spectrometer calibration state 810 to automatically calibrate the sensor using the fixed Spectralon® white reference panel described above. By automating the calibration process, frequent and consistent calibration of the vis-NIR spectrometer is ensured.

Example

A stratified simple random sampling plan was used to select 150 soil core sampling locations in a 600 hectare cattle grazing farm located in Northern NSW (S30.69, E151.48), using an approach similar to that described in Viscarra Rossel, R. A., Brus, D., Lobsey, C., Shi, Z., McLachlan, G., 2016, *Baseline estimates of soil organic carbon by proximal sensing: Comparing design-based, model-assisted and model-based inference*, Geoderma 265, 152-163. doi:dx-.doi.org/10.1016/j.geoderma.2015.11.016). The soil measurement system was used to measure the properties of all 150 soil cores, but for conciseness only the measurements made on two soil cores are presented here, as shown in FIGS. 29 and 30, respectively.

The soil cores were sampled using a Geoprobe® 7822DT core sampling rig and the DT325 sampling systems, as described above, and were sampled directly into clear plastic liners with end caps. Immediately before measurement, a longitudinal section of the liner was cut to expose the core surface for vis-NIR measurements and imaging.

The soil core measurement locations were every 2.5 cm intervals from the surface to a depth of 30 cm, and then every 5 cm from 30 to 100 cm depth. Thus, there were a total of 26 measurements per soil core, and the time taken to measure each core was approximately 15 minutes (i.e., each measurement took approximately 35 seconds).

Figure 20:
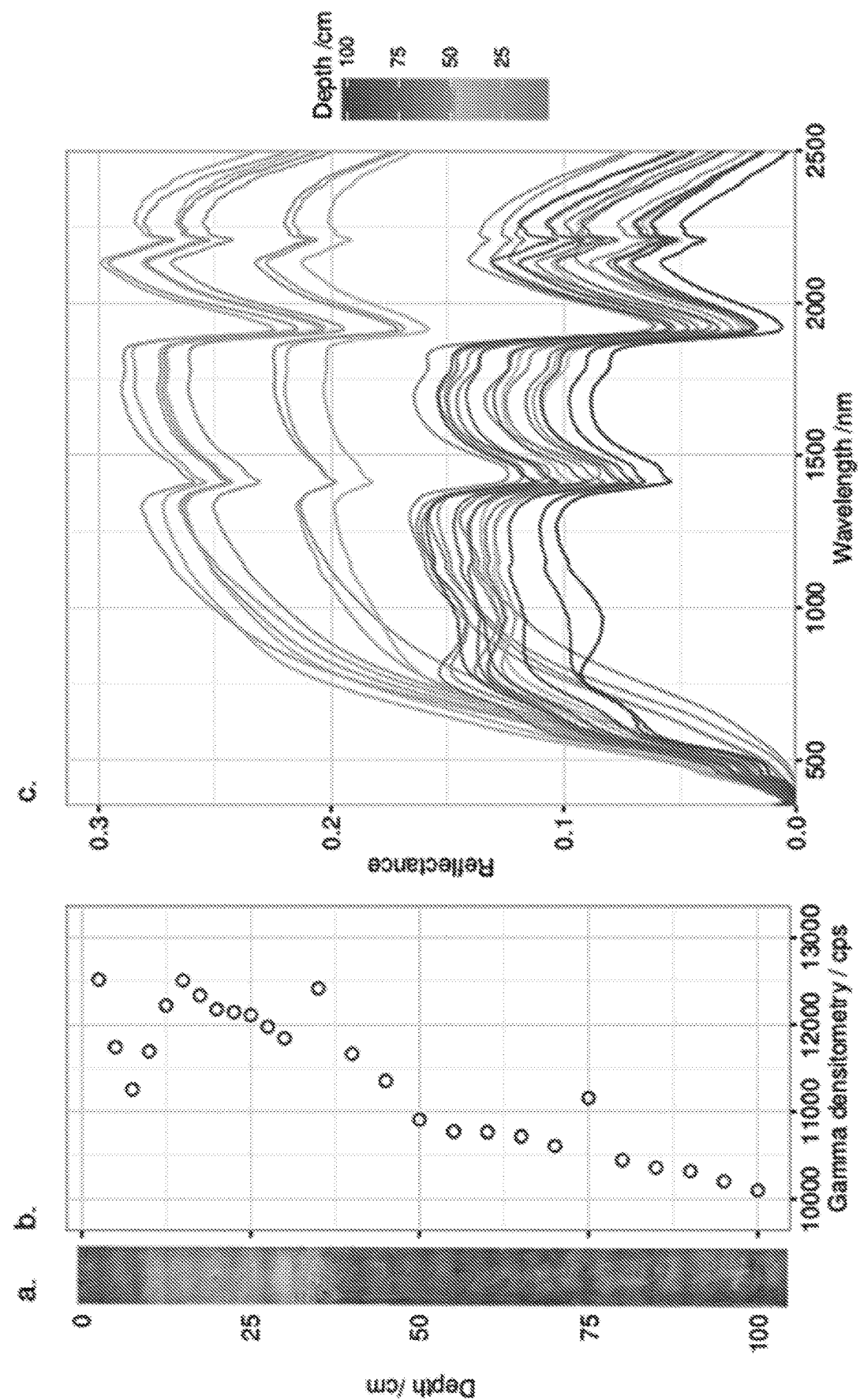
FIG. 20 includes an acquired photographic image along a soil core (extreme left), a corresponding depths profile of gamma rays passing through the soil core to the gamma ray detector (indicative of bulk density), and corresponding visible-NIR spectra acquired at different depths along the soil core (and used to estimate water content and other soil properties at different depths)

FIG. 20 includes (moving from left to right) a true colour image of a soil core (vertical strip to the extreme left), which is useful for making visual inspection and for record-keeping, a graph of the soil core density as a function of depth along the soil core, and a graph showing the vis-NIR reflectance spectra measured at each sampling depth. The density values are in (essentially arbitrary) units of detector counts per second (cps) as generated by the gamma ray attenuation sensor, and the reflectance spectra were generated from the vis-NIR spectrometer.

The soil cores were under field conditions and not entirely dry. Thus, before using the vis-NIR spectra with the spectroscopic modelling (Table 1), they were corrected using the EPO method described above to remove the effects of water on the spectra. The DS method (also described above) was used to remove the effects of water before measuring the Fe and clay mineralogy of the cores. In this case, DS was used because, unlike EPO, it does not alter the corrected spectra.

Spectroscopic modelling was used to predict the soil property depth profiles using both the Australian spectral libraries and rs-local, as described above. Using the spectra of the 150 soil cores, a representative set of 20 local soil samples was selected for laboratory analyses. The selection was made using the Kennard-Stone algorithm (Kennard, R. W., Stone, L. A., 1969, *Computer aided design of experiments*, Technometrics 11, 137-148) as described in Lobsey I 2016. The 20 samples were analysed for soil organic C by total combustion using a LECO carbon analyser (as described in Rayment, G., Lyons, D., 2011, *Soil chemical methods—Australasia*, CSIRO Publishing, Collingwood, Victoria), particulate, humic and resistant C using the nuclear magnetic resonance (NMR) method (as described in Baldock, J. A., Sanderman, J., Macdonald, L. M., Puccini, A., Hawke, B., Szarvas, S., McGowan, J., 2013, *Quantifying the allocation of soil organic carbon to biologically significant fractions*, Soil Research 51, 561-576. doi:10.1071/SR12374).

12 local surface soil samples from a previous reconnaissance survey were analysed for clay content using the hydrometer method (as described in Gee, G., Bauder, J., 1986. Particle size analysis, in: Klute, A. (Ed.), *Methods of Soil Analysis*, Part 1, 2nd edition ed. American Society of Agronomy and Soil Science Society of America, Madison, Wis., USA. Agronomy Monograph no. 9, pp. 383-411) and pH in a 1:5 water suspension (as described in Rayment, G., Lyons, D., 2011. Soil chemical methods—Australasia. CSIRO Publishing, Collingwood, Victoria).

The contents of particulate, humic and resistant organic C were predicted using the organic C fractions library described in Viscarra Rossel, R. A., Hicks, W. S., 2015, *Soil organic carbon and its fractions estimated by visible-near infrared transfer functions*, European Journal of Soil Science 66, 438-450. doi:10.1111/ejss.12237). θ, CEC and AWC were predicted using only the Australian soil vis-NIR library because no local measurements of these properties were available. All of the spectroscopic models were assessed using a 10-fold cross validation.

Using specific absorptions in the vis-NIR, the relative abundances of goethite, which was the dominant iron oxide in the soil of this farm, and the clay minerals kaolinite, illite and smectite (see above) were determined.

Figure 21:
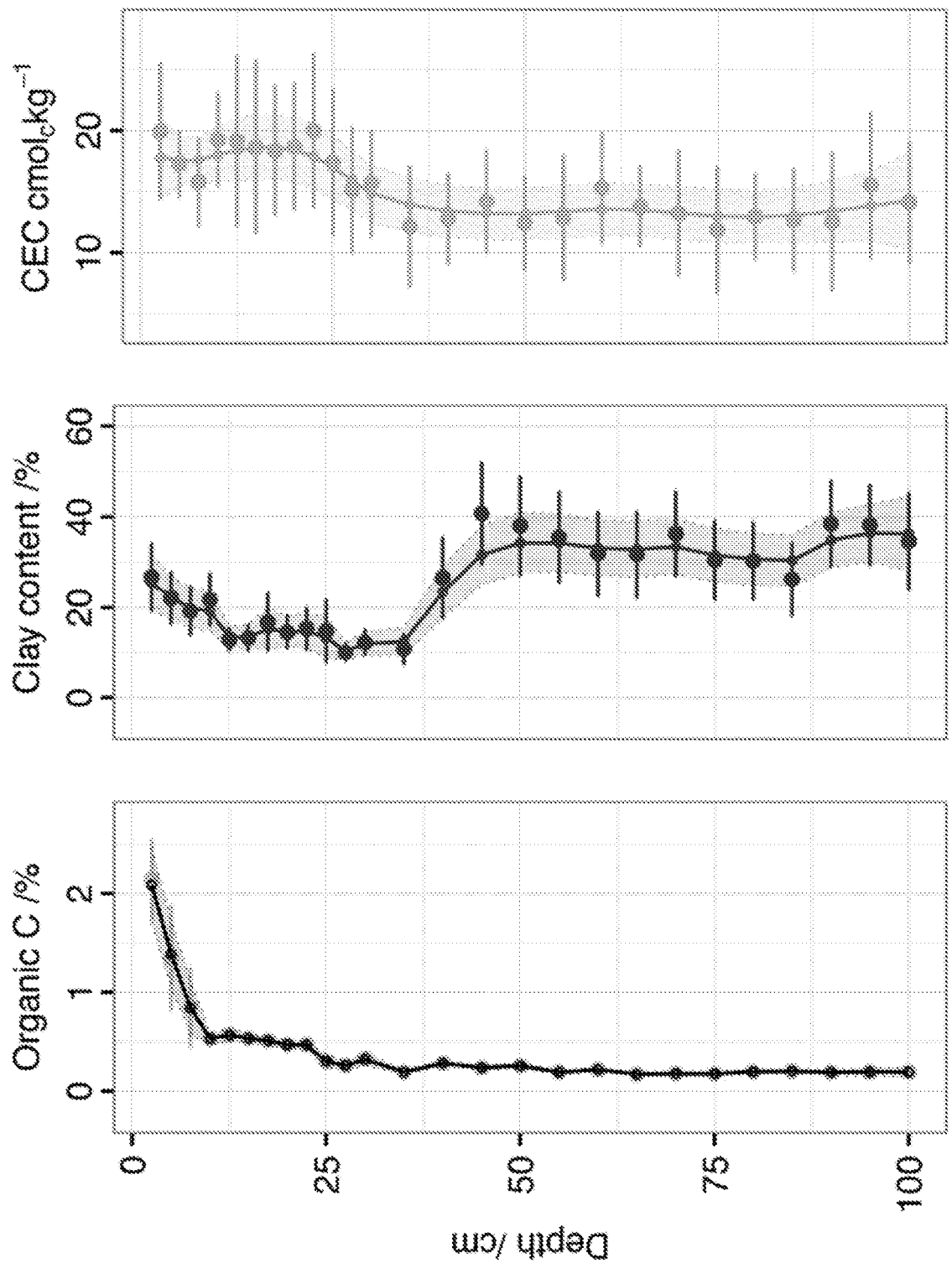
FIG. 21 is a set of graphs of cation exchange capacity (CEC), clay content, and organic carbon content and uncertainties as a function of depth along a soil core, demonstrating the filtering of the soil property profiles and their improved accuracy, as determined by the system.

FIG. 21 shows the results of the Kalman smoothing, with depth profiles of organic C, clay, and CEC compared to the unfiltered discrete spectroscopic measurements (discs with 95% confidence lines), the Kalman estimates provide continuous profile estimates with narrower uncertainties.

The uncertainties of the estimates of organic C down the profile are small because the spectroscopic models with rs-local were derived using a representative set of data. The estimates of clay content are more accurate at the soil surface above 30 cm because the models with rs-local used a local set of 12 surface samples. Thus, below 30 cm the estimates are more uncertain, as shown in FIG. 21. There were no local samples to help with the modelling of CEC. The spectroscopic models were derived using the Australian soil spectral library and so the uncertainties are relatively large throughout the profile (FIG. 21).

Figure 22:
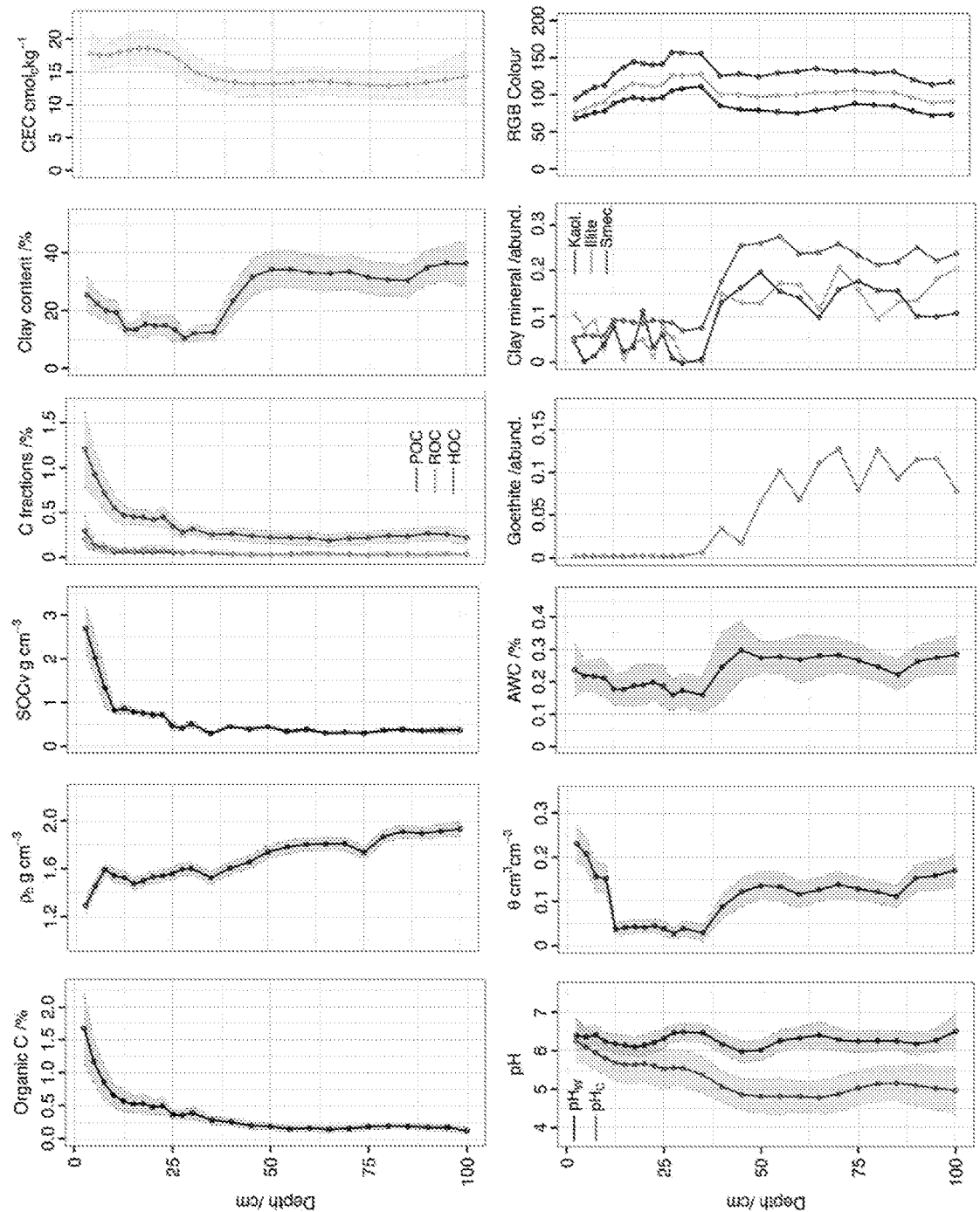
FIGS. 22 and 23 are respectively first and second sets of 14 graphs of various soil properties as a function of depth for particular first and second soil cores, respectively, as determined by the system.
Figure 23:
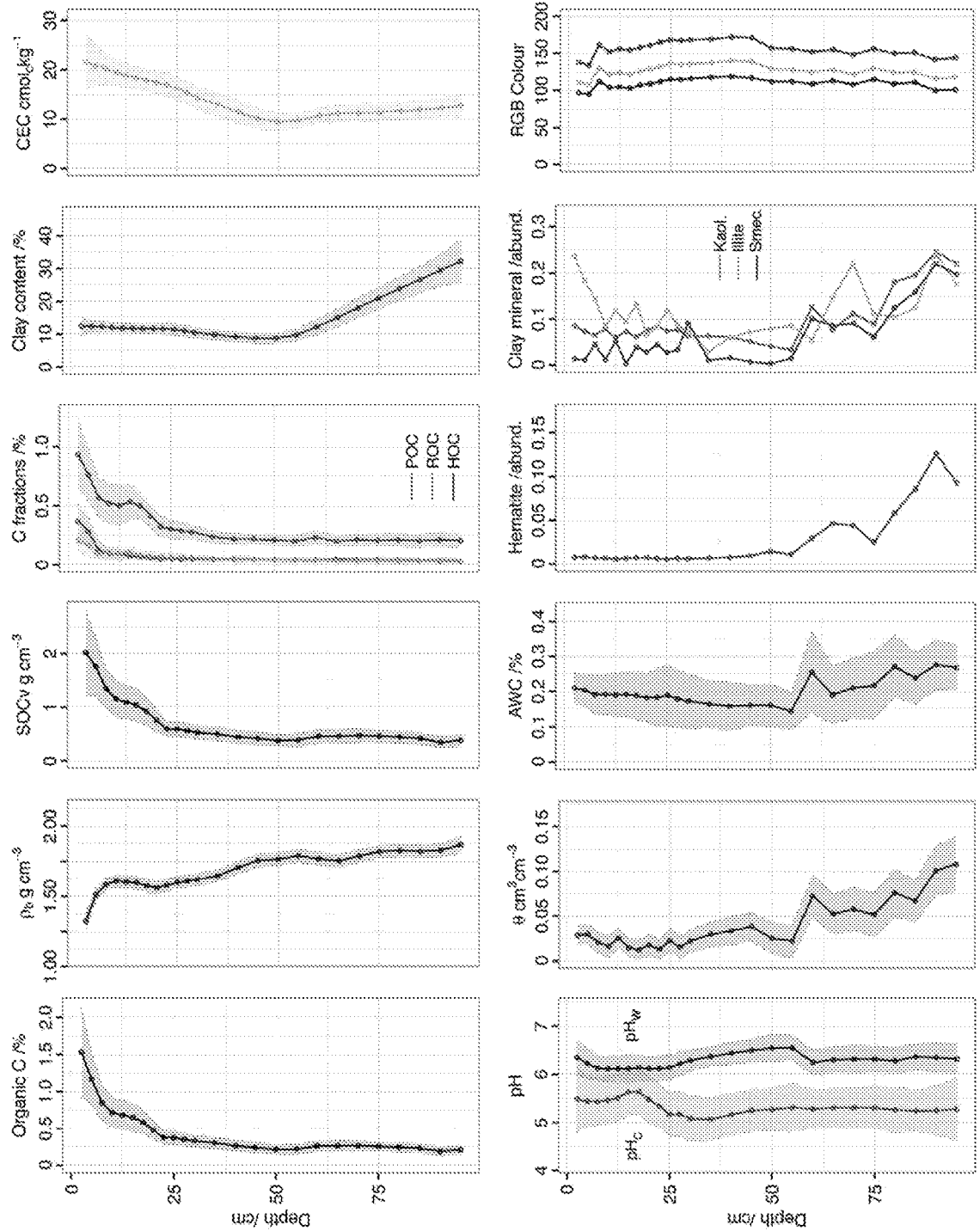

Each of FIGS. 22 and 23 is a set of graphs of the continuous soil property profiles generated from a corresponding single soil core of the study site. The volumetric soil organic C content (SOCv) profile was determined as the product of the organic C content (%) and bulk density profiles.

Many modifications will be apparent to those skilled in the art without departing from the scope of the present invention.

The invention claimed is:

1. A soil condition analysis system, including:
a support platform to support an elongate soil core extracted from the Earth;
a plurality of soil sensing components configured to measure corresponding characteristics of a soil core supported on the support platform, including a camera to image the soil core, an optical spectrometer to measure light from the soil core at near-infrared and/or mid-infrared wavelengths, and a gamma ray attenuation component to measure attenuation of gamma-rays transmitted through the soil core;
one or more data acquisition components in communication with the soil sensing components and configured to generate measurement data representing the measured characteristics from the soil sensing components; and
a data processing component configured to process the measurement data to generate soil property data representing corresponding soil properties of the elongate soil core as a function of depth, based on spectroscopic models representing relationships between the soil properties and the measured characteristics;
wherein at least one of the support platform and the plurality of soil sensing components is mounted on a computer-controlled translation stage to enable the soil sensing components to automatically measure the corresponding characteristics of the soil core at mutually spaced locations along a longitudinal axis of the elongate soil core;
wherein the data processing component is configured to generate estimates of the bulk density of the soil core as a function of depth from the measured attenuation of gamma rays through the soil core and the measured water content of the soil core by compensating for the absorption of the gamma rays by the water content of the soil core to generate estimates of the bulk density of the soil core without the water content;
wherein the water content of the soil core is determined from spectroscopic modelling of visible-near infrared spectra measured from the soil core.

2. The soil condition analysis system of claim 1, wherein the soil sensing components include a long wave infrared (LWIR) camera.

3. The soil condition analysis system of claim 1, wherein the soil sensing components include an x-ray sensor component to measure x-ray fluorescence of the soil or x-ray transmission through the soil core.

4. The soil condition analysis system of claim 1, wherein the soil sensing components include at least one of a microwave soil water sensing component and a laser induced breakdown spectroscopy (LIBS) sensing component.

5. The soil condition analysis system of claim 1, including a display component to display, during data acquisition, a visual image of at least a corresponding portion of the soil core, together with measurement data being acquired from at least one other of the soil sensing components.

6. The soil condition analysis system of claim 1, wherein the soil properties includes at least five of: soil organic carbon, organic carbon composition (particulate, humic, and resistant carbon), bulk density, soil carbon stocks, soil water, available water capacity, clay content, total nitrogen, iron mineralogies, clay mineralogies, soil colour, cation exchange capacity, and pH.

7. The soil condition analysis system of claim 1, wherein the spectroscopic models are generated by machine learning applied to a soil spectral library of previously measured soil spectra and corresponding soil properties.

8. The soil measurement system of claim 1, wherein the spectroscopic models are generated by analysing a representative subset of a plurality of soil cores taken from a common geographic region to be analysed to determine the soil properties of the subset of soil cores by laboratory analysis, and associating the determined soil properties with corresponding spectra from the subset of soil cores; using the relationships between the determined soil properties and corresponding spectra to customise a soil spectral library of previously measured soil spectra and corresponding soil properties by removing those members of the soil spectral library that are least representative of the subset of soil cores and adding the determined soil properties and corresponding spectra of the subset of soil cores to the remaining members of the soil spectral library to provide a soil spectral library customised to the common geographic region; and generating the spectroscopic models from the customised soil spectral library.

9. The soil measurement system of claim 8, wherein the members of the soil spectral library are removed by iteratively removing corresponding members of the soil spectral library that are least representative of the subset of soil cores as determined by a corresponding partial least squares regression performed in each iteration.

10. The soil measurement system of claim 9, wherein a fixed proportion of the remaining number of members of the soil spectral library are removed in each iteration.

11. The soil measurement system of claim 8, wherein the representative subset of soil cores is selected by the Kennard-Stone method.

12. The soil condition analysis system of claim 1, wherein the support platform, soil analysis components, and data acquisition components are mounted on a trailer such that the system can be transported to a site where soil cores are to be extracted for measurement by the system.

13. A soil condition analysis process, including:
using a soil condition analysis system to generate measurement data representing measured characteristics of an elongate soil core at mutually spaced locations along a longitudinal axis of the elongate soil core by controlling a computer-controlled translation stage to automatically translate at least one of a support platform on which the soil core is supported and a plurality of soil sensing components configured to measure corresponding characteristics of the soil core, the plurality of soil sensing components including a camera to image the soil core, an optical spectrometer to measure light from the soil core at near-infrared and/or mid-infrared wavelengths, and a gamma ray attenuation component to measure attenuation of gamma-rays transmitted through the soil core;
processing the measurement data to generate soil property data representing corresponding soil properties of the elongate soil core as a function of depth, based on spectroscopic models representing relationships between the soil properties and the measured characteristics, including determining water content of the soil core from spectroscopic modelling of visible-near infrared spectra measured from the soil core; and generating estimates of the bulk density of the soil core from the measured attenuation of gamma rays through the soil core and the determined water content of the soil core by compensating for the absorption of the gamma rays by the water content of the soil core to generate estimates of the bulk density of the soil core without the water content.

14. The soil condition analysis process of claim 13, including applying machine learning to a soil spectral library of previously measured soil spectra and corresponding soil properties to generate the spectroscopic models.

15. The soil condition analysis process of claim 13, wherein the spectroscopic models are generated by analysing a representative subset of a plurality of soil cores taken from a common geographic region to be analysed to determine the soil properties of the subset of soil cores by laboratory analysis, and associating the determined soil properties with corresponding spectra from the subset of soil cores; using the relationships between the determined soil properties and corresponding spectra to customise a soil spectral library of previously measured soil spectra and corresponding soil properties by removing those members of the soil spectral library that are least representative of the subset of soil cores and adding the determined soil properties and corresponding spectra of the subset of soil cores to the remaining members of the soil spectral library to provide a soil spectral library customised to the common geographic region; and generating the spectroscopic models from the customised soil spectral library.

16. The soil condition analysis process of claim 15, wherein the customising of the soil spectral library includes iteratively removing members of the soil spectral library that are least representative of the subset of soil cores as determined by a partial least squares regression.

17. The soil condition analysis process of claim 16, wherein a fixed proportion of the remaining number of members of the soil spectral library are removed in each iteration.

18. The soil condition analysis process of claim 15, wherein the representative subset of soil cores is selected by the Kennard-Stone method.

19. The soil condition analysis process of claim 13, wherein the soil properties includes at least five of: soil organic carbon, organic carbon composition (particulate, humic and resistant organic carbon), bulk density, soil carbon stocks, soil water, available water capacity, clay content, total nitrogen, iron mineralogies, clay mineralogies, soil colour, cation exchange capacity, and pH.

20. At least one computer-readable storage medium having stored thereon executable instructions that, when executed by at least one processor of a data processing system, cause the at least one processor to execute the process of claim 13.

* * * * *